United States Patent
Heiliger

(10) Patent No.: US 12,064,131 B2
(45) Date of Patent: *Aug. 20, 2024

(54) DRIVE AND ARTICULATION MECHANISMS FOR SURGICAL INSTRUMENTS FOR USE IN ROBOTIC SURGICAL SYSTEMS

(71) Applicant: Covidien LP, Mansfield, MA (US)

(72) Inventor: Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 176 days.

This patent is subject to a terminal disclaimer.

(21) Appl. No.: 17/735,149

(22) Filed: May 3, 2022

(65) Prior Publication Data

US 2022/0257273 A1 Aug. 18, 2022

Related U.S. Application Data

(63) Continuation of application No. 16/749,000, filed on Jan. 22, 2020, now Pat. No. 11,331,113.

(51) Int. Cl.
*A61B 17/29* (2006.01)
*A61B 34/00* (2016.01)
(Continued)

(52) U.S. Cl.
CPC .............. *A61B 17/29* (2013.01); *A61B 34/71* (2016.02); *A61B 2017/2936* (2013.01); *A61B 2017/320094* (2017.08); *A61B 2018/00077* (2013.01); *A61B 2018/0063* (2013.01); *A61B 18/085* (2013.01); *A61B 18/1445* (2013.01);
(Continued)

(58) Field of Classification Search
CPC ......... A61B 17/29; A61B 34/71; A61B 34/35; A61B 2017/320094; A61B 2017/2936; A61B 18/085; A61B 18/1445; A61B 2018/00077; A61B 2018/0063;
(Continued)

(56) References Cited

U.S. PATENT DOCUMENTS

| 5,752,973 A | 5/1998 | Kieturakis |
| 5,792,135 A | 8/1998 | Madhani et al. |

(Continued)

FOREIGN PATENT DOCUMENTS

| CN | 1662174 A | 8/2005 |
| EP | 3689282 A1 | 8/2020 |

(Continued)

OTHER PUBLICATIONS

Extended European Search Report issued in corresponding application EP 21152626.4 dated Jul. 7, 2021 (8 pages).

*Primary Examiner* — Brooke Labranche
(74) *Attorney, Agent, or Firm* — Carter, DeLuca & Farrell LLP

(57) ABSTRACT

A gearbox assembly for a surgical instrument includes an articulation sub-assembly and a jaw drive sub-assembly. The articulation sub-assembly is configured to articulate an end effector of the surgical instrument and the jaw drive sub-assembly is configured to move jaw members of the end effector between an open and closed position. The articulation sub-assembly includes two input shafts, a proximal plate, a middle plate, two center gears, and four lead screws with four nuts. The jaw drive sub-assembly includes a drive rod coupled to at least one of the jaws and a spring force assembly to maintain a force between the jaws.

20 Claims, 20 Drawing Sheets

(51) Int. Cl.
  *A61B 17/32* (2006.01)
  *A61B 18/00* (2006.01)
  *A61B 18/08* (2006.01)
  *A61B 18/14* (2006.01)
  *A61B 18/18* (2006.01)
  *A61B 34/35* (2016.01)

(52) U.S. Cl.
  CPC ............... *A61B 2018/1455* (2013.01); *A61B 2018/1807* (2013.01); *A61B 2018/1861* (2013.01); *A61B 34/35* (2016.02)

(58) Field of Classification Search
  CPC .... A61B 2018/1455; A61B 2018/1807; A61B 2018/1861
  See application file for complete search history.

(56) References Cited

U.S. PATENT DOCUMENTS

| | | |
|---|---|---|
| 5,848,986 A | 12/1998 | Lundquist et al. |
| 6,817,974 B2 | 11/2004 | Cooper et al. |
| 7,799,028 B2 | 9/2010 | Schechter et al. |
| 7,861,906 B2 | 1/2011 | Doll et al. |
| 7,918,230 B2 | 4/2011 | Whitman et al. |
| 8,579,176 B2 | 11/2013 | Smith et al. |
| 9,055,961 B2 | 6/2015 | Manzo et al. |
| 9,474,569 B2 | 10/2016 | Manzo et al. |
| 11,331,113 B2 | 5/2022 | Heiliger |
| 2002/0099371 A1 | 7/2002 | Schulze et al. |
| 2002/0177842 A1 | 11/2002 | Weiss |
| 2003/0125734 A1 | 7/2003 | Mollenauer |
| 2003/0208186 A1 | 11/2003 | Moreyra |
| 2006/0022015 A1 | 2/2006 | Shelton et al. |
| 2006/0025811 A1 | 2/2006 | Shelton |
| 2007/0233052 A1 | 10/2007 | Brock |
| 2008/0015631 A1 | 1/2008 | Lee et al. |
| 2010/0274265 A1 | 10/2010 | Wingardner et al. |
| 2010/0292691 A1 | 11/2010 | Brogna |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2020/0237453 A1 | 7/2020 | Anglese |
| 2020/0261167 A1 | 8/2020 | Anglese |

FOREIGN PATENT DOCUMENTS

| | | |
|---|---|---|
| EP | 3695800 A1 | 8/2020 |
| JP | H0549647 A | 3/1993 |
| JP | 2008546503 A | 12/2008 |
| WO | 2007002180 A2 | 1/2007 |
| WO | 2017053363 A1 | 3/2017 |

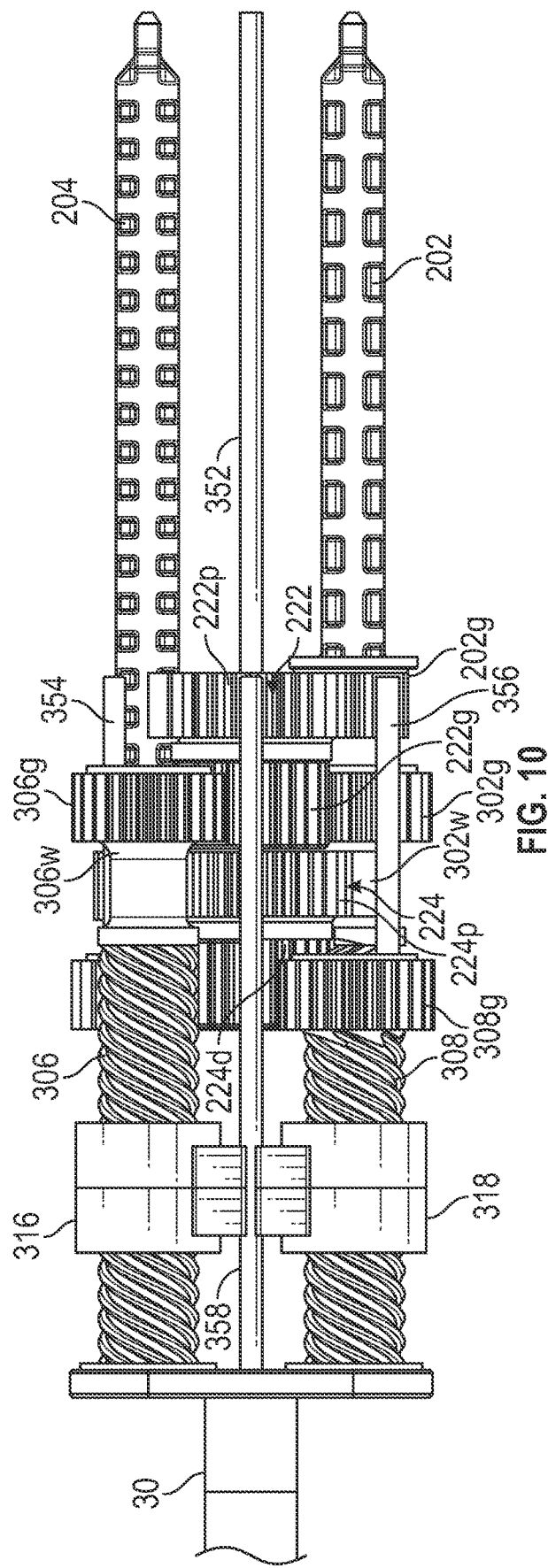
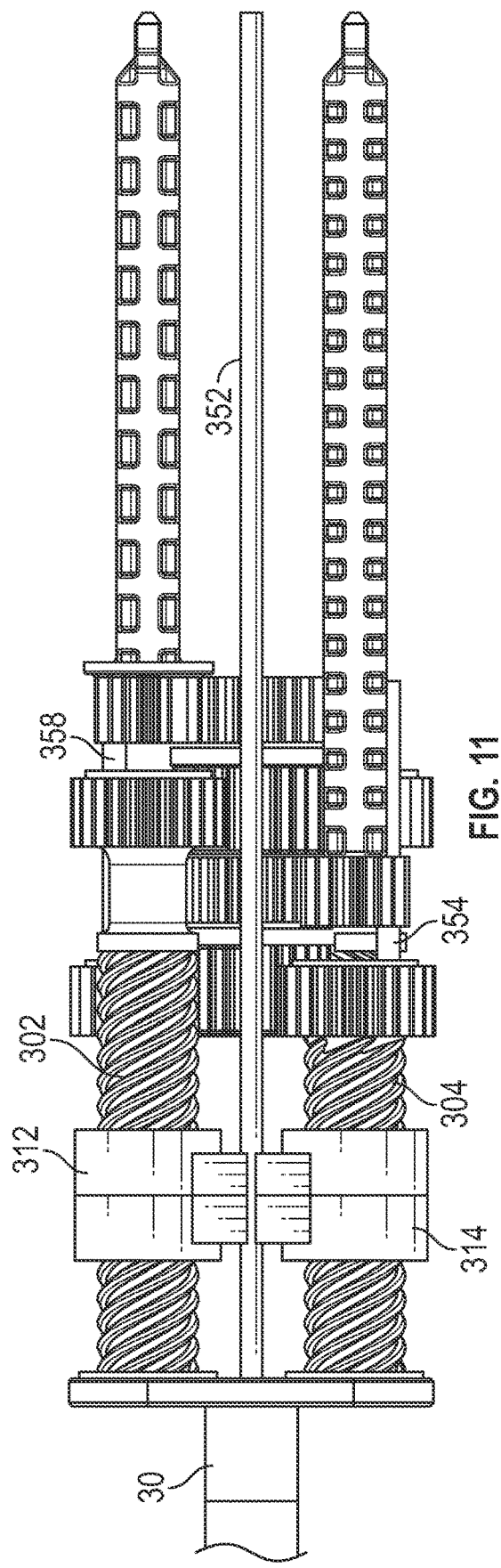

1

DRIVE AND ARTICULATION MECHANISMS FOR SURGICAL INSTRUMENTS FOR USE IN ROBOTIC SURGICAL SYSTEMS

CROSS-REFERENCE TO RELATED APPLICATIONS

The present application is a continuation application of U.S. application Ser. No. 16/749,000, filed on Jan. 22, 2020, the entire contents of which are incorporated by reference herein.

FIELD

The present disclosure relates to surgical instruments and, more specifically, to drive and articulation mechanisms for surgical instruments such as, for example, for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The number, type, and configuration of inputs provided by the robotic arm of a robotic surgical system are constraints in the design of surgical instruments configured for use with the robotic surgical system. That is, in designing a surgical instrument compatible for mounting on and use with the robotic arm of a robotic surgical system, consideration should be given as to how to utilize the available inputs provided by the robotic arm to achieve the desired functionality of the surgical instrument.

SUMMARY

As used herein, the term "distal" refers to the portion that is being described which is further from a surgeon, while the term "proximal" refers to the portion that is being described which is closer to a surgeon. The terms "about," substantially," and the like, as utilized herein, are meant to account for manufacturing, material, environmental, use, and/or measurement tolerances and variations. Further, to the extent consistent, any of the aspects described herein may be used in conjunction with any or all of the other aspects described herein.

Provided in accordance with aspects of the present disclosure is a surgical instrument including a housing, a shaft extending from the housing, and end effector coupled to a distal portion of the shaft, and a gearbox assembly disposed within the housing. The gearbox assembly includes an articulation sub-assembly configured to articulate the end effector about a longitudinal axis defined by the shaft. The articulation sub-assembly includes a first lead screw including a gear portion, a waist portion, and an elongate threaded body portion, and a second lead screw including a gear portion and an elongate threaded body portion. A first nut is threadingly engaged with the elongate threaded body portion of the first lead screw such that rotation of the first lead screw effects longitudinal translation of the first nut. A second nut is threadingly engaged with the elongate threaded body portion of the second lead screw such that rotation of the second lead screw effects longitudinal translation of the second nut. The articulation sub-assembly further includes a middle plate including a middle plate stem extending proximally therefrom and a proximal center gear and a distal center gear coupled to the middle plate stem. Each of the proximal center gear and the distal center gear includes a proximal gear portion and a distal gear portion. The distal gear portion of the proximal center gear is meshingly engaged with the gear portion of the first lead screw. Additionally, the distal gear portion of the distal center gear is meshingly engaged with the gear portion of the second lead screw and the proximal gear portion of the distal center gear is aligned with the waist portion of the first lead screw.

In an aspect, the articulation sub-assembly includes a first input shaft and a second input shaft. The first input shaft includes a gear portion meshingly engaged with the proximal gear portion of the proximal center gear such that rotation of the first input shaft causes rotation of the proximal center gear and the first lead screw. The second input shaft includes a first input shaft including a gear portion meshingly engaged with the proximal gear portion of the proximal center gear such that rotation of the first input shaft causes rotation of the proximal center gear and the first lead screw.

In an aspect, the articulation sub-assembly includes a proximal plate aligning the first input shaft with the first lead screw.

In an aspect, the middle plate aligns the second input shaft with the second lead screw.

In an aspect, the surgical instrument includes articulation cables including respective distal ends coupled to the end effector and respective proximal ends each coupled to one of the first nut and the second nut such that longitudinal translation of the first nut and the second nut causes articulation of the end effector.

In an aspect, the surgical instrument includes a first guide bar and a second guide bar disposed within the housing. The first guide bar is operably coupled to the middle plate and the first nut and is configured to inhibit rotation of the first nut relative to the first lead screw. The second guide bar is operably coupled to the middle plate and the second nut and is configured to inhibit rotation of the second nut relative to the second lead screw.

In an aspect, the articulation sub-assembly includes a third lead screw and a third nut. The third lead screw includes a gear portion, a waist portion, and an elongate threaded body portion. The gear portion of the third lead screw is meshingly engaged with the distal gear portion of the proximal center gear and the waist portion of the third lead screw is aligned with the proximal gear portion of the distal center gear. The third nut is threadingly engaged with the elongate threaded body portion of the third lead screw such that rotation of the third lead screw effects longitudinal translation of the third nut.

In an aspect, the articulation sub-assembly includes a fourth lead screw and a fourth nut. The fourth lead screw includes a gear portion and an elongate threaded body portion. The gear portion of the fourth lead screw is meshingly engaged with the distal gear portion of the distal center gear. The fourth nut is threadingly engaged with the elongate threaded body portion of the fourth lead screw such that rotation of the fourth lead screw effects longitudinal translation of the fourth nut.

In an aspect, the surgical instrument includes a third guide bar and a fourth guide bar disposed within the housing. The third guide bar is operably coupled to the middle plate and the third nut and is configured to inhibit rotation of the third nut relative to the third lead screw. The fourth guide bar is operably coupled to the middle plate and the fourth nut and is configured to inhibit rotation of the fourth nut relative to the fourth lead screw.

In an aspect, the end effector includes a first jaw member and a second jaw member, where the first jaw member is movable relative to the second jaw member between an open position and a closed position to grasp tissue therebetween. Additionally, in an aspect, the gearbox assembly further includes a jaw drive sub-assembly operably coupled to at least one of the first jaw member or the second jaw member and configured to move the first jaw member relative to the second jaw member between the open position and the closed position.

In an aspect, the jaw drive sub-assembly includes a drive rod operably coupled to at least one of the first jaw member or the second jaw member and a spring force assembly releasably coupled to the drive rod. The spring force assembly includes a proximal hub defining an elongate hub stem, a compression spring disposed around the elongate hub stem, a distal hub disposed around a distal portion of the compression spring and movable relative to the proximal hub, and a lock plate slidingly coupled to the proximal hub and configured to releasably lock the drive rod to the proximal hub.

In an aspect, a distal portion of the elongate hub stem includes a wing extending radially outward therefrom and the distal hub defines a shelf configured to engage the wing to inhibit distal translation of the distal hub beyond the wing thereby defining a maximum distance between the proximal hub and the distal hub.

In an aspect, the jaw drive sub-assembly includes an input shaft having an elongate threaded body portion threadingly engaged with a threaded bore of the distal hub such that rotation of the input shaft causes longitudinal translation of the distal hub.

In an aspect, the proximal hub includes a retainer guide and the distal hub includes a retainer guide. Each of the retainer guide of the proximal hub and the retainer guide of the distal hub is configured to operably couple to a guide bar to inhibit rotation of the distal hub relative to the proximal hub.

In an aspect, the spring force assembly is configured to maintain a jaw force between the first jaw member and the second jaw member during articulation of the end effector.

In an aspect, a proximal portion of the drive rod includes a key and the lock plate defines a key hole configured to receive the key to releasably secure the drive rod to the proximal hub.

Also provided in accordance with aspects of the present disclosure is a gearbox assembly for use with surgical instrument including an end effector having a first jaw member and a second jaw member. The gearbox assembly includes an articulation sub-assembly configured to articulate the end effector and a jaw drive sub-assembly configured to transition the end effector between an open position and a closed position. The articulation sub-assembly includes a first lead screw including a gear portion, a waist portion, and an elongate threaded body portion and a second lead screw including a gear portion and an elongate threaded body portion. A first nut is threadingly engaged with the elongate threaded body portion of the first lead screw such that rotation of the first lead screw effects longitudinal translation of the first nut. A second nut is threadingly engaged with the elongate threaded body portion of the second lead screw such that rotation of the second lead screw effects longitudinal translation of the second nut. The articulation sub-assembly further includes a middle plate including a middle plate stem extending proximally therefrom and a proximal center gear and a distal center gear coupled to the middle plate stem. Each of the proximal center gear and the distal center gear includes a proximal gear portion and a distal gear portion. The distal gear portion of the proximal center gear is meshingly engaged with the gear portion of the first lead screw. Additionally, the distal gear portion of the distal center gear is meshingly engaged with the gear portion of the second lead screw and the proximal gear portion of the distal center gear is aligned with the waist portion of the first lead screw. Additionally, the jaw drive sub-assembly includes a drive rod operably coupled to at least one of the first jaw member or the second jaw member and a spring force assembly releasably coupled to the drive rod. The spring force assembly includes a proximal hub defining an elongate hub stem, a compression spring disposed around the elongate hub stem, a distal hub disposed around a distal portion of the compression spring and movable relative to the proximal hub, and a lock plate slidingly coupled to the proximal hub and configured to releasably lock the drive rod to the proximal hub.

In an aspect, the spring force assembly is configured to maintain a jaw force between the first jaw member and the second jaw member during articulation of the end effector.

In an aspect, the gearbox assembly includes a guide bar operably coupled to the articulation sub-assembly and the jaw drive sub-assembly and configured to maintain alignment therebetween.

In an aspect, the articulation sub-assembly includes a first input shaft and a second input shaft. The first input shaft includes a gear portion meshingly engaged with the proximal gear portion of the proximal center gear such that rotation of the first input shaft causes rotation of the proximal center gear and the first lead screw. The second input shaft includes a first input shaft including a gear portion meshingly engaged with the proximal gear portion of the proximal center gear such that rotation of the first input shaft causes rotation of the proximal center gear and the first lead screw.

BRIEF DESCRIPTION OF THE DRAWINGS

Various aspects and features of the present disclosure are described hereinbelow with reference to the drawings wherein like numerals designate identical or corresponding elements in each of the several views.

FIG. 10 is a bottom view of the articulation sub-assembly of FIG. 4 with parts removed;

FIG. 11 is a top view of the articulation sub-assembly of FIG. 4 with parts removed;

DETAILED DESCRIPTION

Figure 1A:
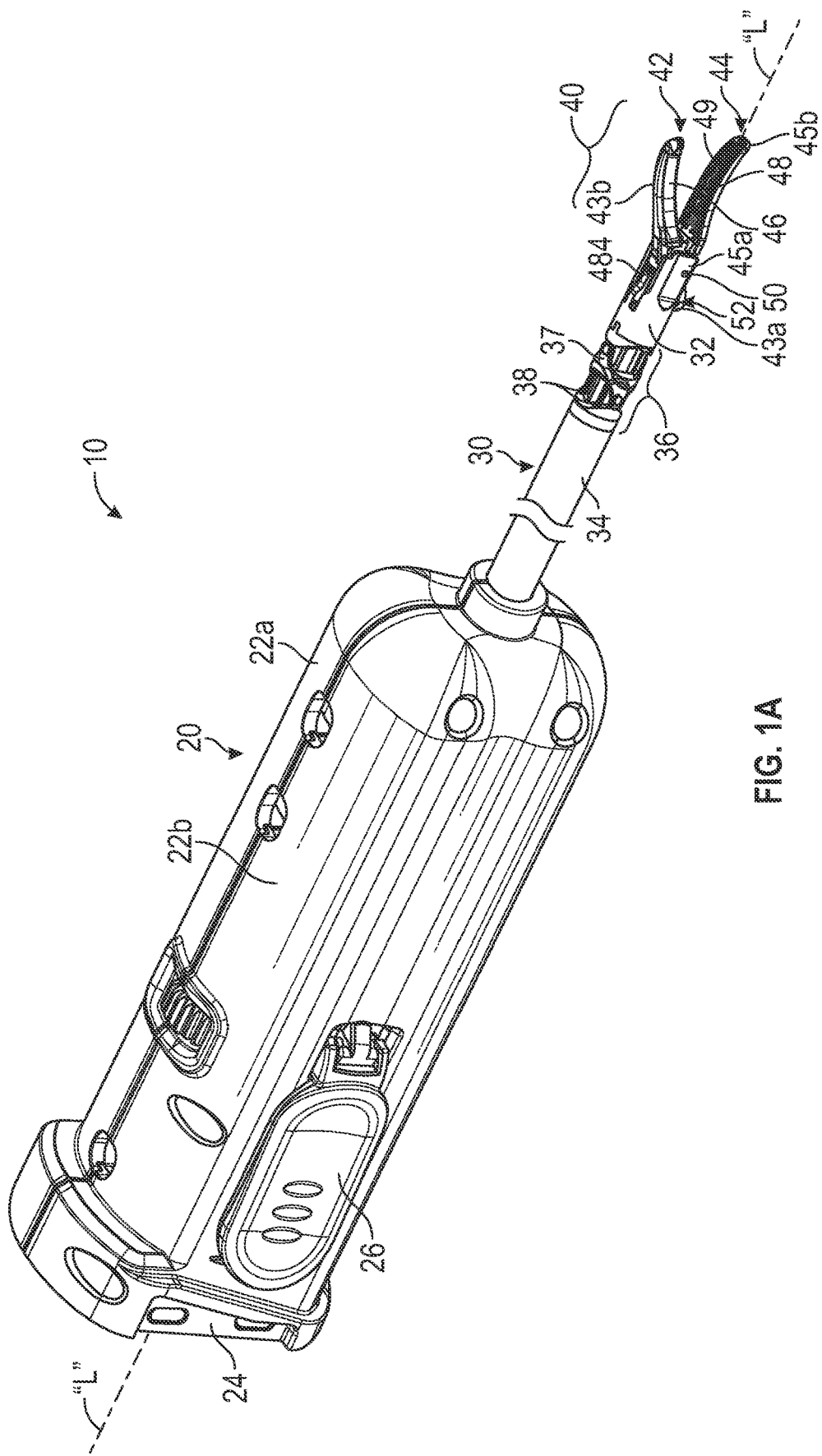
FIG. 1A is a perspective view of a surgical instrument provided in accordance with the present disclosure configured for mounting on a robotic arm of a robotic surgical system.
Figure 1B:
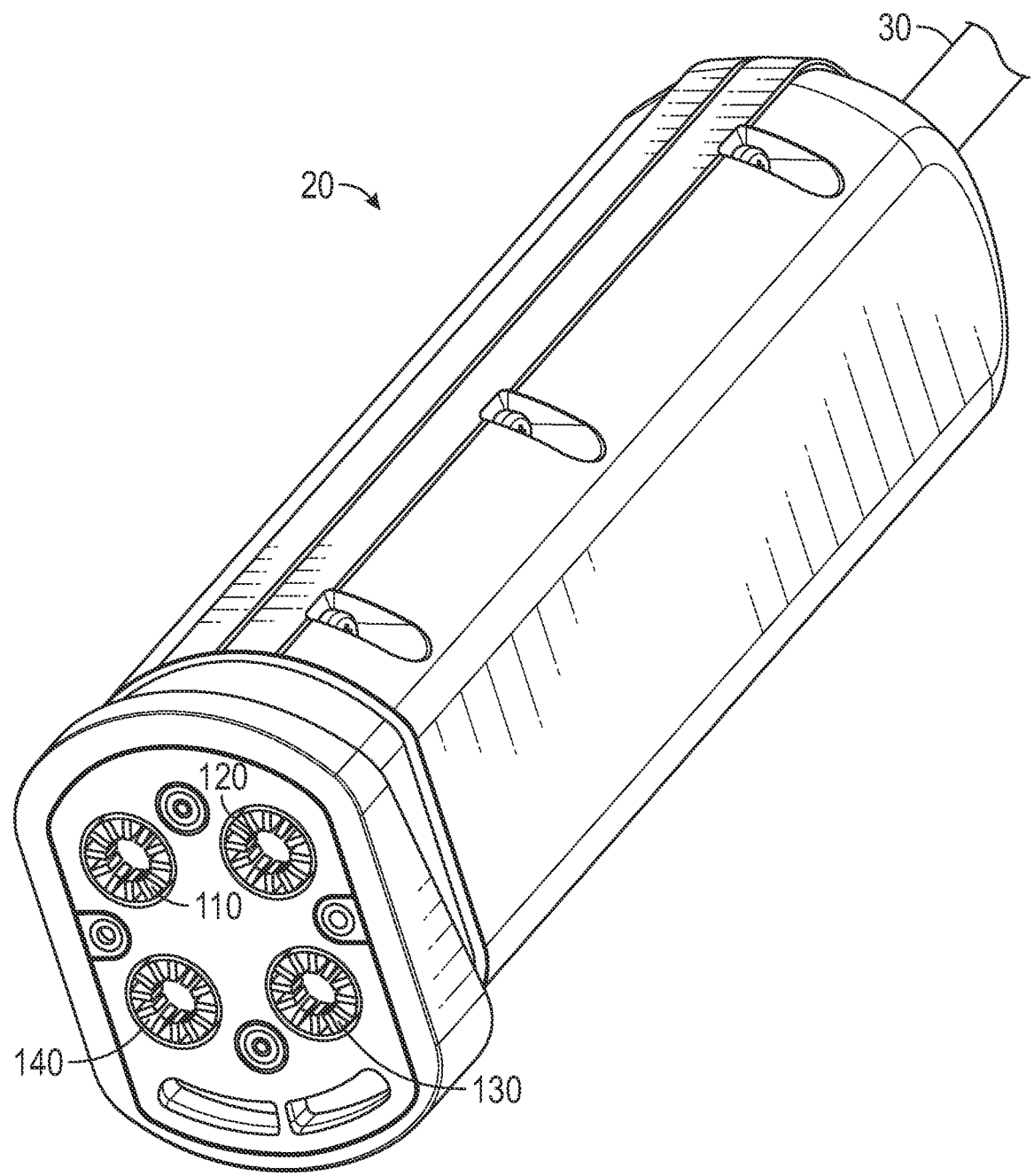
FIG. 1B is a rear, perspective view of a proximal portion of the surgical instrument of FIG. 1A.
Figure 2:
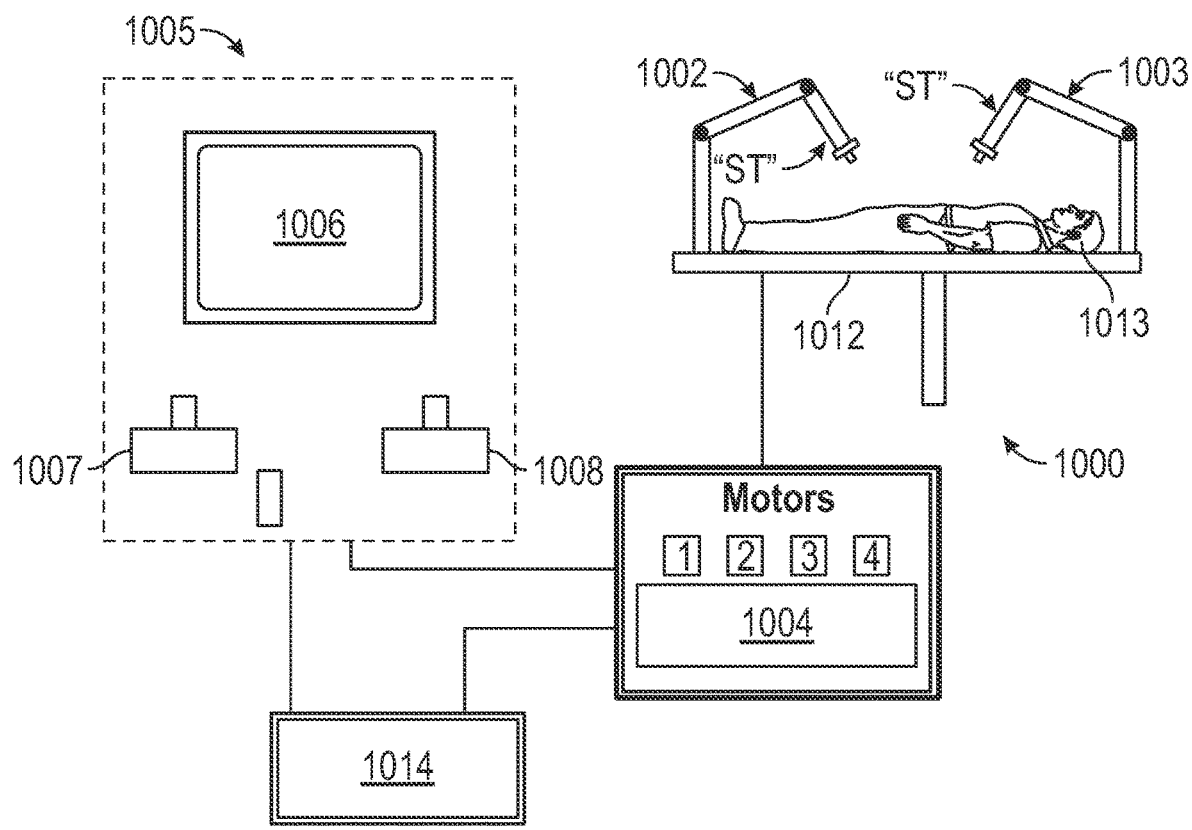
FIG. 2 is a schematic illustration of an exemplary robotic surgical system configured to releasably receive the surgical instrument of FIG. 1A.

Referring to FIGS. 1A, 1B, 2, and 3, a surgical instrument 10 provided in accordance with the present disclosure generally includes a housing 20, a shaft 30 extending distally from housing 20, an end effector assembly 40 extending distally from shaft 30, and a gearbox assembly 100 disposed within housing 20 and operably associated with end effector assembly 40. Instrument 10 is detailed herein as an articulating electrosurgical forceps configured for use with a robotic surgical system, e.g., robotic surgical system 1000 (FIG. 2). However, the aspects and features of instrument 10 provided in accordance with the present disclosure, detailed below, are equally applicable for use with other suitable surgical instruments and/or in other suitable surgical systems.

With particular reference to FIG. 1A, housing 20 of instrument 10 includes first and second body portion 22a, 22b and a proximal face plate 24 that cooperate to enclose gearbox assembly 100 (FIG. 3) therein. Proximal face plate 24 includes apertures defined therein through which inputs 110, 120, 130, 140 (FIG. 1B) of gearbox assembly 100 extend for coupling to drivers of a robotic surgical system 1000 (FIG. 2). A pair of latch levers 26 (only one of which is illustrated in FIG. 1A) extend outwardly from opposing sides of housing 20 and enable releasable engagement of housing 20 with a robotic arm of a surgical system, e.g., robotic surgical system 1000 (FIG. 2).

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extend through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation sub-assembly 200 of gearbox assembly 100 to enable selective articulation of distal segment 32 (and, thus end effector assembly 40) relative to proximal segment 34 and housing 20, e.g., about at least two axes of articulation (yaw and pitch articulation, for example).

With respect to articulation of end effector assembly 40 relative to proximal segment 34 of shaft 30, actuation of articulation cables 38 is done in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

Continuing with reference to FIG. 1A, end effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively. Such a configuration enables pivoting of jaw member 42 relative to jaw member 44 and distal segment 32 of shaft 30 between a spaced-apart position (e.g., an open position of end effector assembly 40) and an approximated position (e.g., a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

In aspects, longitudinally-extending knife channels 49 (only knife channel 49 of jaw member 44 is illustrated; the knife channel of jaw member 42 is similarly configured) are defined through tissue-contacting surfaces 46, 48, respectively, of jaw members 42, 44. In such aspects, a knife assembly including a knife tube (not shown) extending from housing 20 through shaft 30 to end effector assembly 40 and a knife blade (not shown) disposed within end effector assembly 40 between jaw members 42, 44 is provided to enable cutting of tissue grasped between tissue-contacting surfaces 46, 48 of jaw members 42, 44, respectively.

Referring still to FIG. 1A, a distal portion of a drive rod 484 is operably coupled to cam-slot assembly 52 of end effector assembly 40, e.g., engaged with the cam pin thereof, such that longitudinal actuation of drive rod 484 pivots jaw member 42 relative to jaw member 44 between the spaced-apart (e.g., open) and approximated (e.g., closed) positions. More specifically, urging drive rod 484 proximally pivots jaw member 42 relative to jaw member 44 towards the approximated (e.g., closed) position while urging drive rod 484 distally pivots jaw member 42 relative to jaw member 44 towards the spaced-apart (e.g., open) position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into housing 20 wherein drive rod 484 is operably coupled with a jaw drive sub-assembly 400 (FIG. 3) of gearbox assembly 100 to enable selective actuation of end effector assembly 40 to grasp tissue therebetween and apply a closure force within an appropriate jaw closure force range, as detailed below.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, ultrasound, etc., through tissue grasped therebetween for energy-based tissue treatment. Instrument 10 defines a conductive pathway (not shown) through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator, for supplying energy to tissue-contacting surfaces 46, 48 to treat, e.g., seal, tissue grasped between tissue-contacting surfaces 46, 48.

Figure 3:
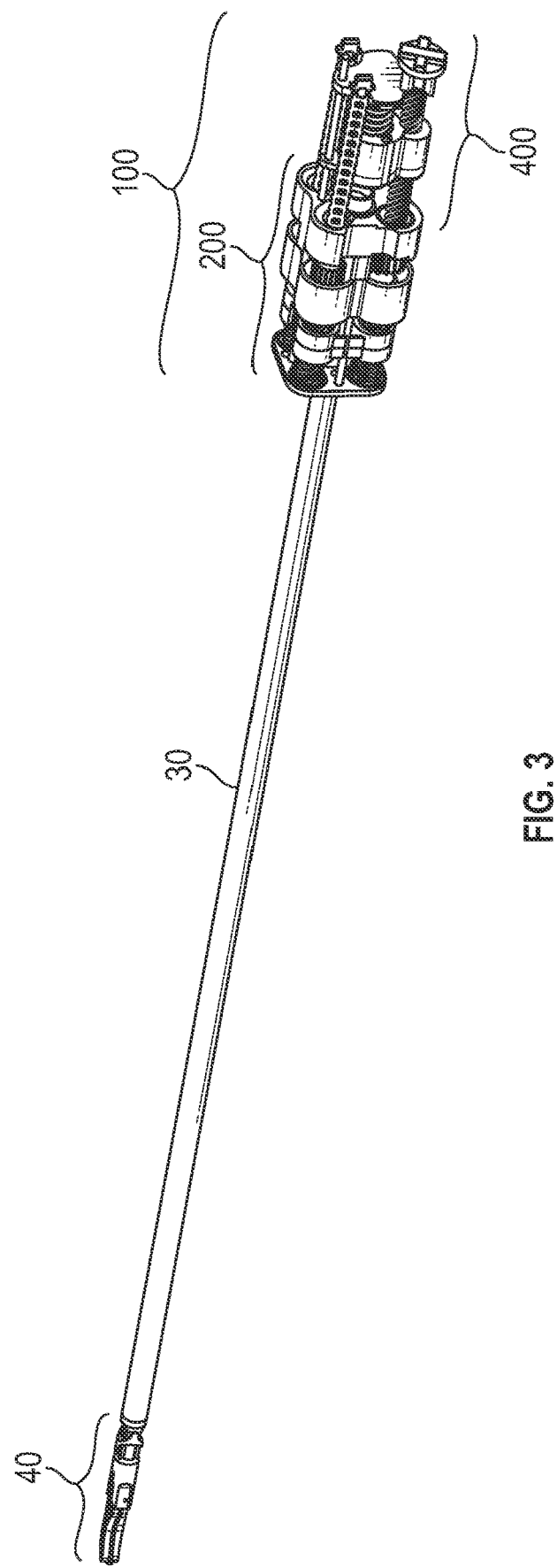
FIG. 3 is a side, perspective view of a gearbox assembly of the surgical instrument of FIG. 1A with an outer shell removed.
Figure 4:
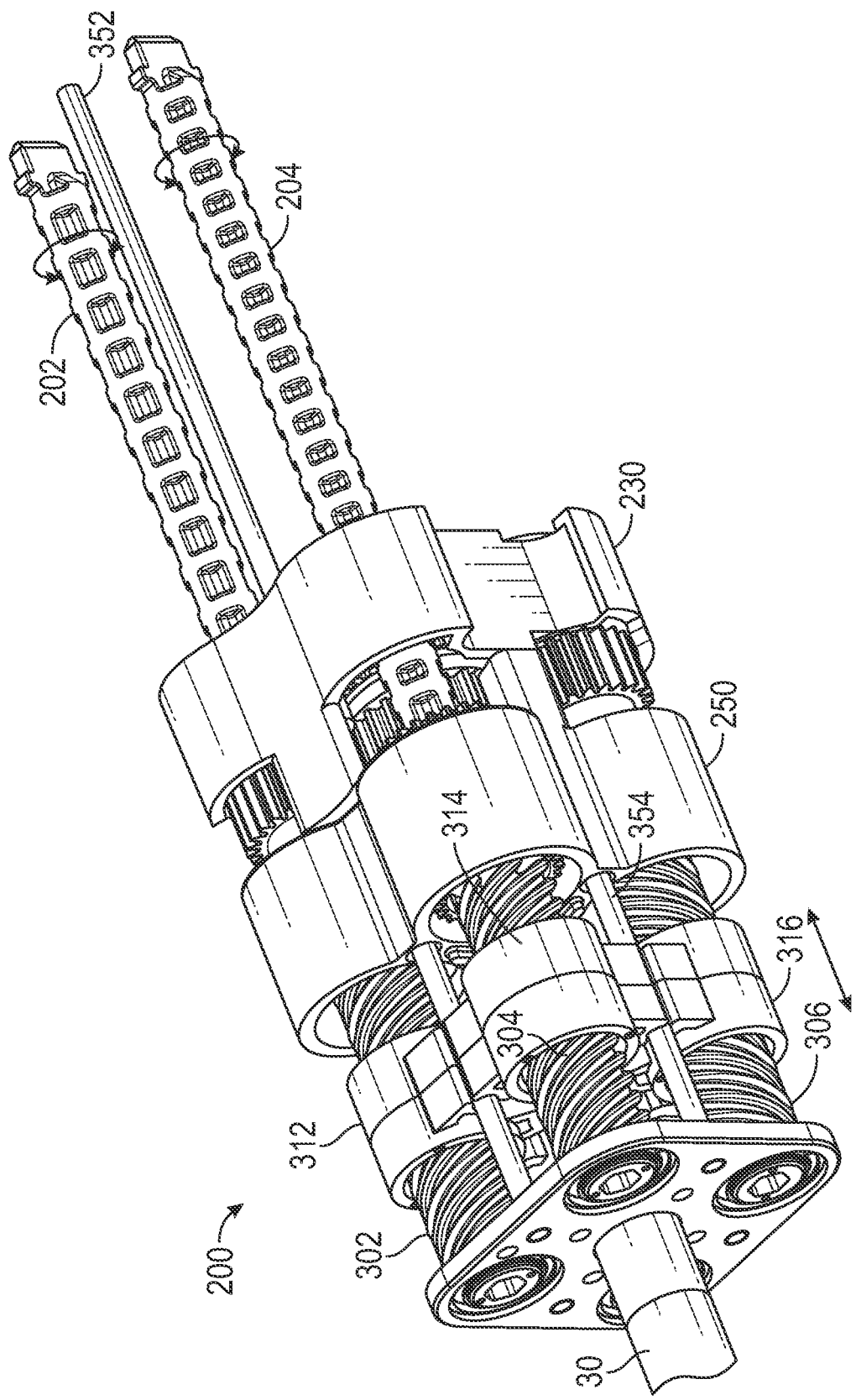
FIG. 4 is a front, perspective view of an articulation sub-assembly of the gearbox assembly of the surgical instrument of FIG. 1A.
Figure 5:
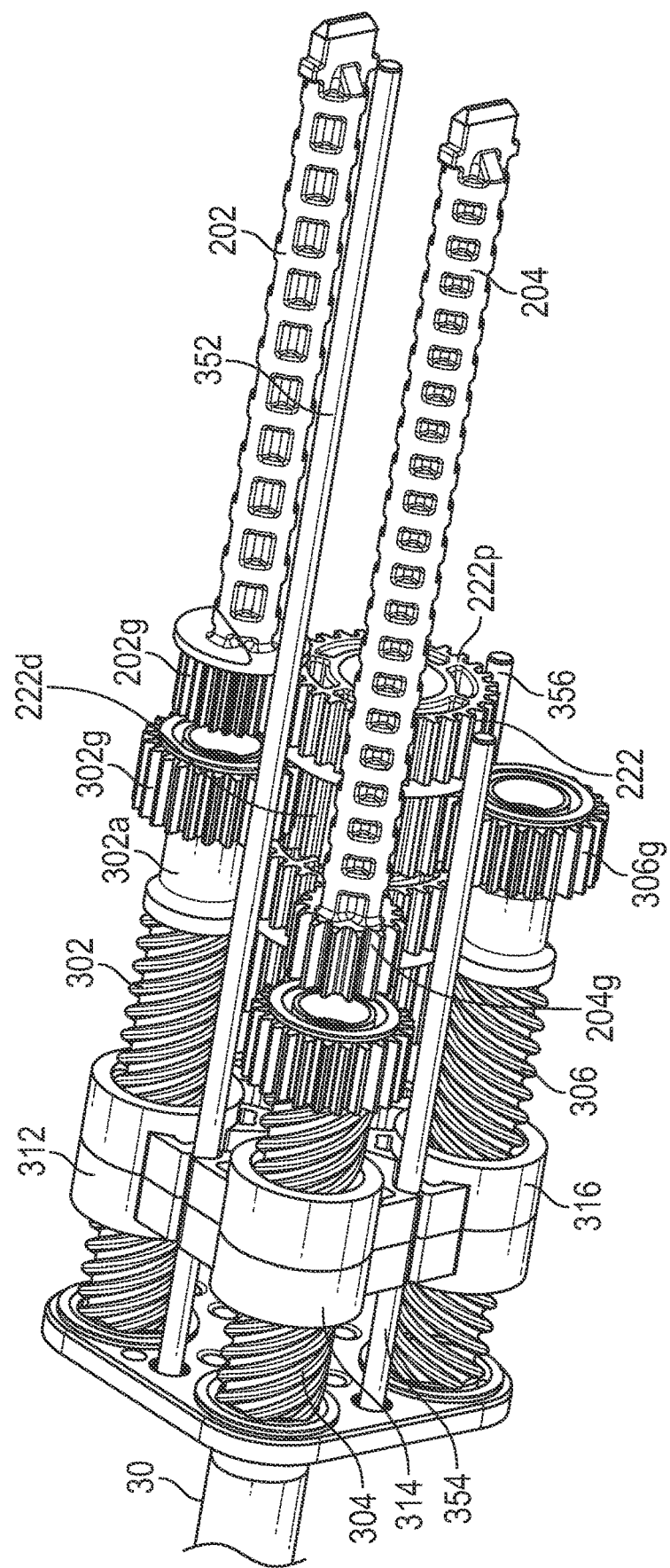
FIG. 5 is a side, perspective view of the articulation sub-assembly of FIG. 4 with parts removed.
Figure 6:
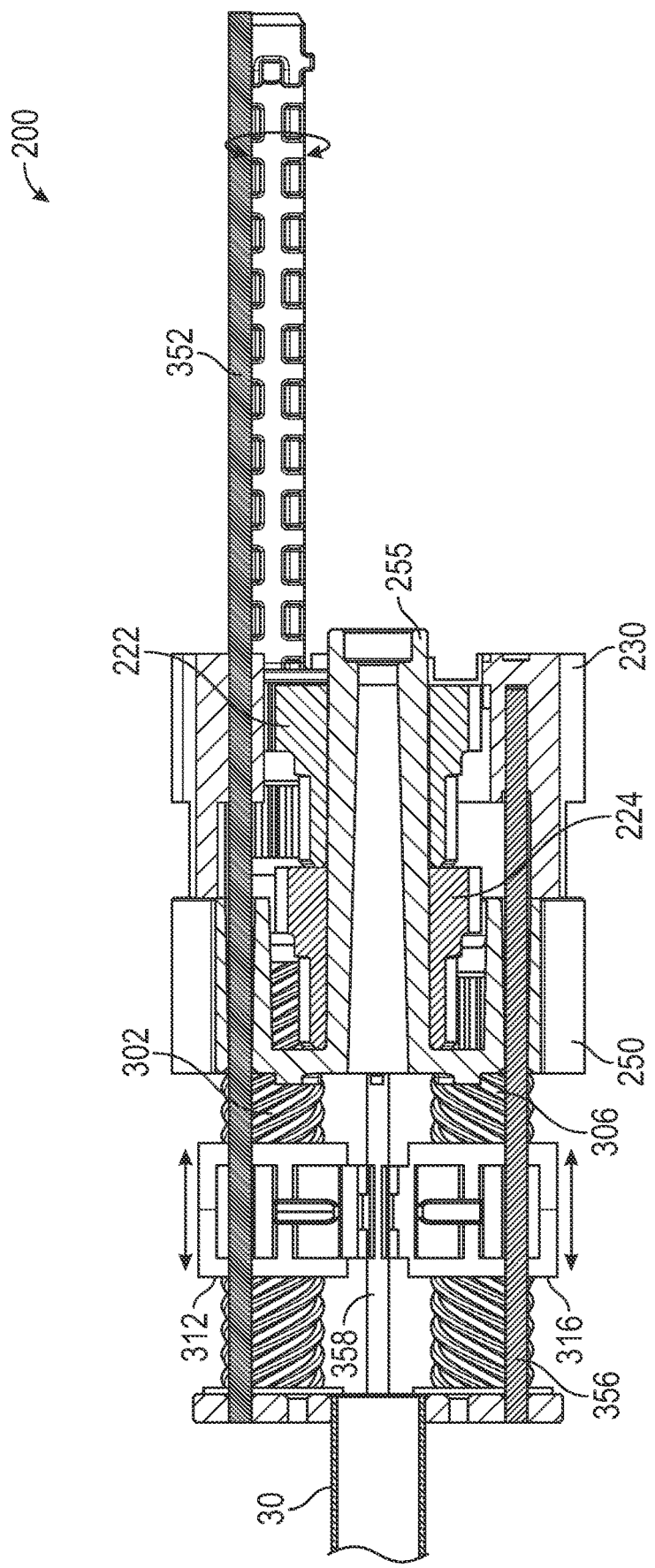
FIG. 6 is a side, cross-sectional view of the articulation sub-assembly of FIG. 4.
Figure 7:
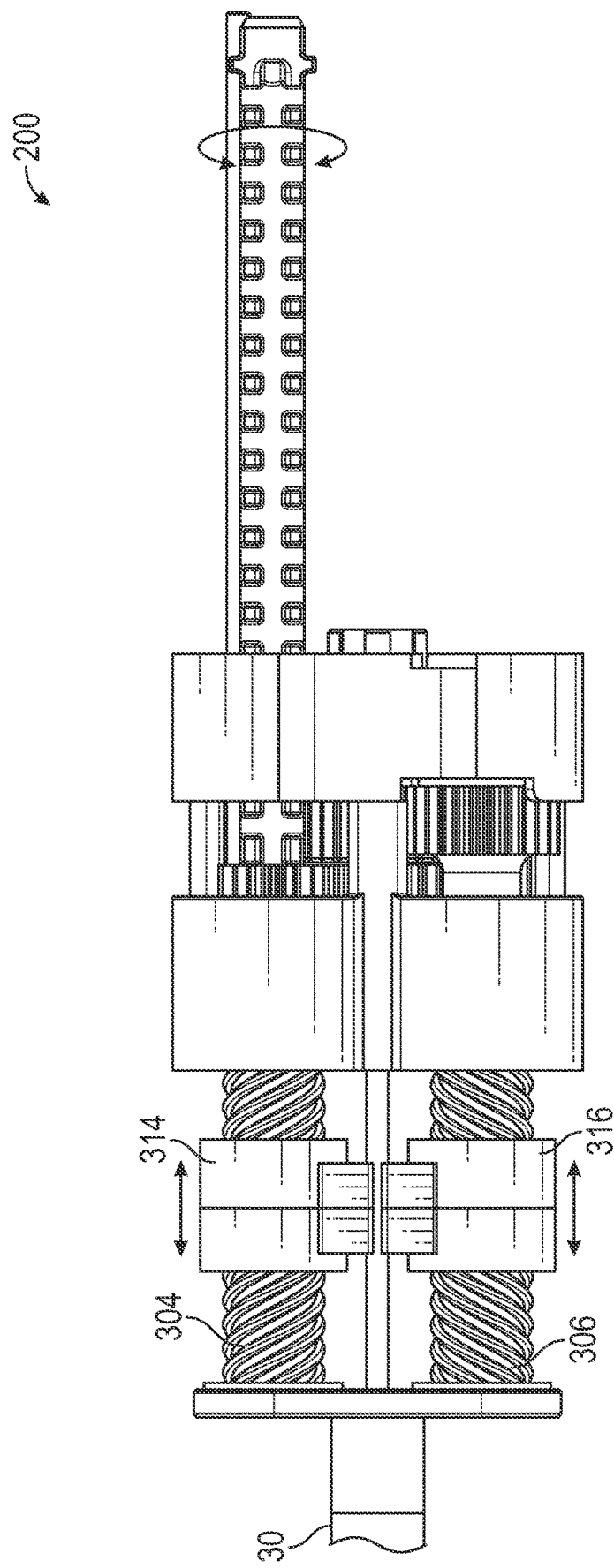
FIG. 7 is a side view of the articulation sub-assembly of FIG. 4.

With reference to FIG. 3, as noted above, gearbox assembly 100 is disposed within housing 20 and includes an articulation sub-assembly 200, a knife drive sub-assembly (not shown), and a jaw drive sub-assembly 400. Articulation sub-assembly 200 is operably coupled between first and second inputs 110, 120 (FIG. 1B), respectively, of gearbox assembly 100 and articulation cables 38 (FIG. 1A) such that, upon receipt of appropriate inputs into first and/or second inputs 110, 120, articulation sub-assembly 200 manipulates cables 38 (FIG. 1A) to articulate end effector assembly 40 in a desired direction relative to a longitudinal axis "L" defined by shaft 30, e.g., to pitch and/or yaw end effector assembly 40.

Knife drive sub-assembly (not shown) is operably coupled between fourth input 140 (FIG. 1B) of gearbox assembly 100 and knife tube (not shown) such that, upon receipt of appropriate input into fourth input 140, knife drive sub-assembly (not shown) reciprocates the knife blade (not shown) between jaw members 42, 44 to cut tissue grasped between tissue-contacting surfaces 46, 48.

Jaw drive sub-assembly 400 is operably coupled between third input 130 (FIG. 1B) of gearbox assembly 100 and drive rod 484 such that, upon receipt of appropriate input into third input 130, jaw drive sub-assembly 400 pivots jaw members 42, 44 between the spaced-apart and approximated positions to grasp tissue therebetween and apply a closure force within an appropriate closure force range.

Gearbox assembly 100 is configured to operably interface with a robotic surgical system 1000 (FIG. 2) when instrument 10 is mounted on robotic surgical system 1000 (FIG. 2), to enable robotic operation of gearbox assembly 100 to provide the above-detailed functionality. That is, robotic surgical system 1000 (FIG. 2) selectively provides inputs to inputs 110, 12, 130, 140 of gearbox assembly 100 to articulate end effector assembly 40, grasp tissue between jaw members 42, 44, and/or cut tissue grasped between jaw members 42, 44. However, it is also contemplated that gearbox assembly 100 be configured to interface with any other suitable surgical system, e.g., a manual surgical handle, a powered surgical handle, etc. For the purposes herein, robotic surgical system 1000 (FIG. 2) is generally described.

Turning to FIG. 2, robotic surgical system 1000 is configured for use in accordance with the present disclosure. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and mounted devices which may be, for example, a surgical tool "ST." One or more of the surgical tools "ST" may be instrument 10 (FIG. 1A), thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Figure 14:
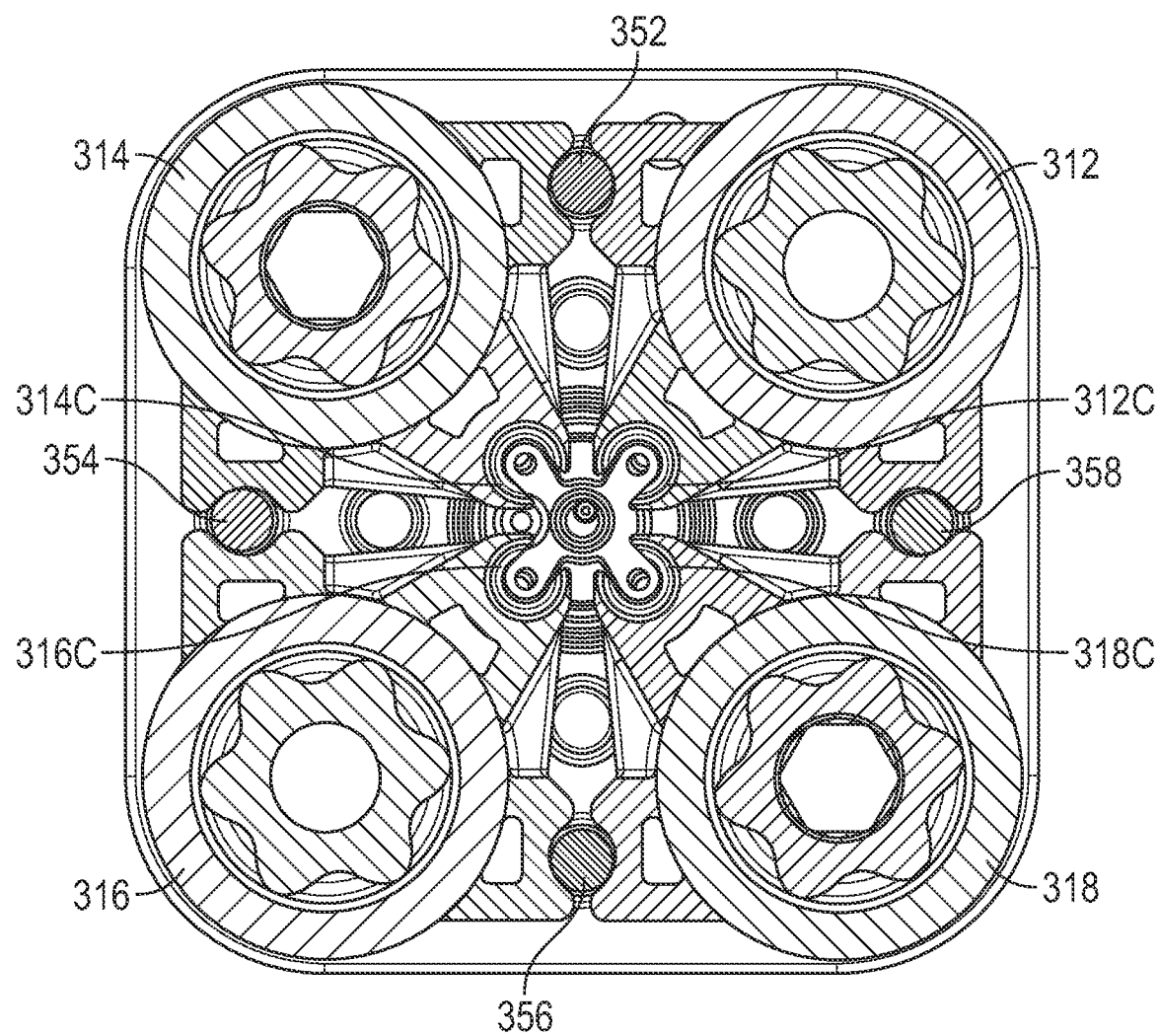
FIG. 14 is a front, cross-sectional view of the articulation sub-assembly of FIG. 4.
Figure 15:
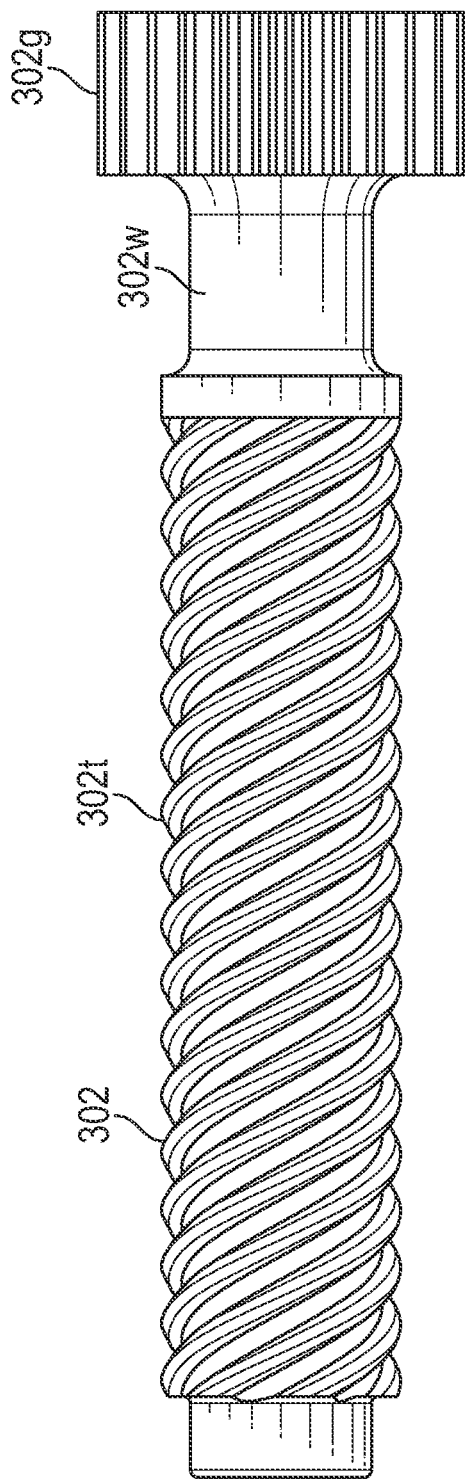
FIG. 15 is a side view of a first drive screw of the articulation sub-assembly of FIG. 4.
Figure 16:
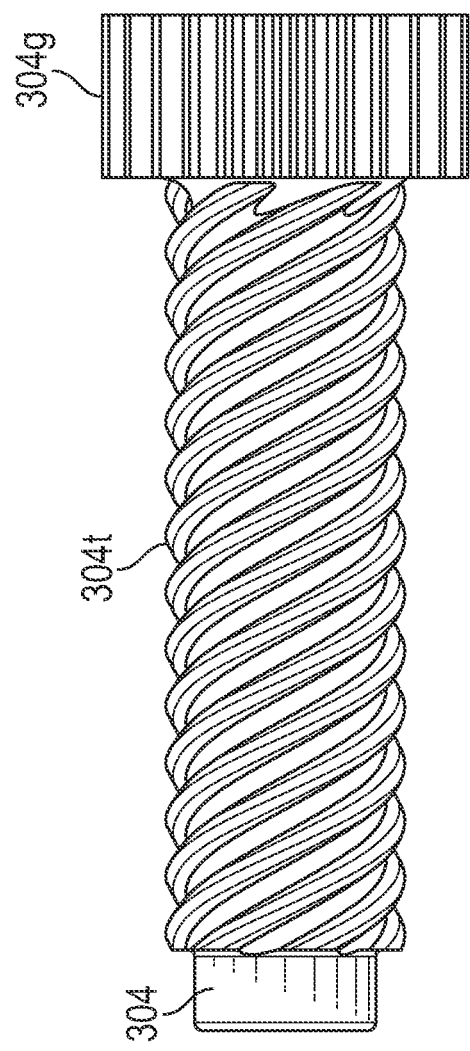
FIG. 16 is a side view of a second drive screw of the articulation sub-assembly of FIG. 4.
Figure 17:
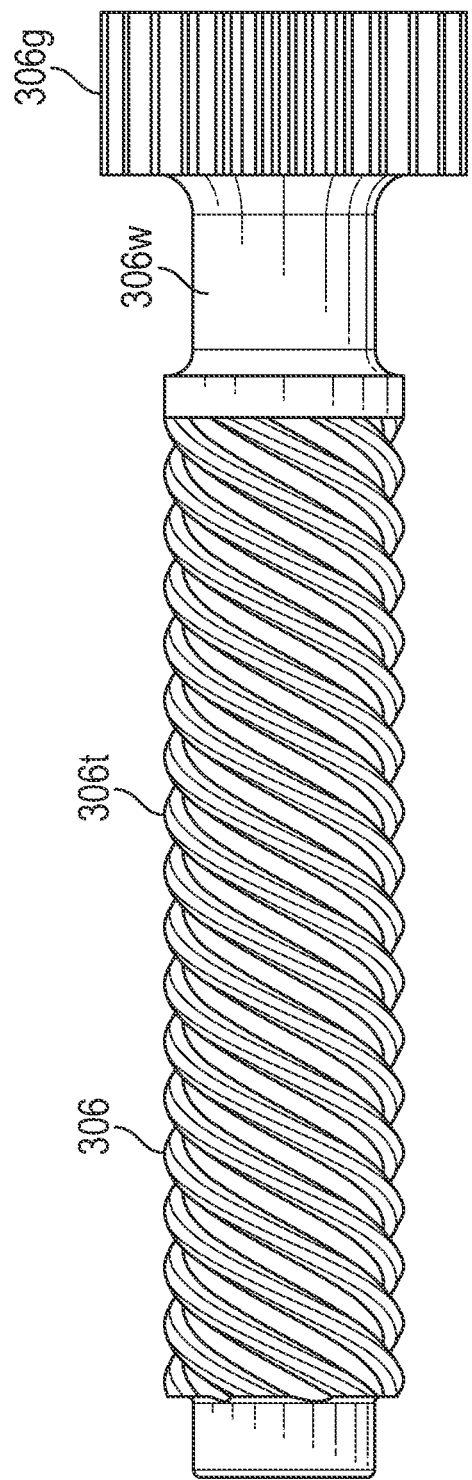
FIG. 17 is a side view of a third drive screw of the articulation sub-assembly of FIG. 4.
Figure 18:
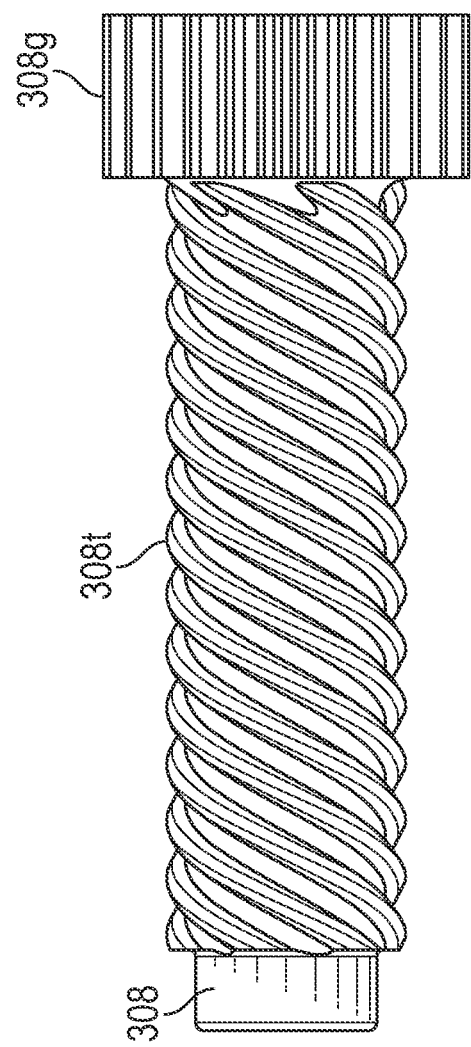
FIG. 18 is a side view of a fourth drive screw of the articulation sub-assembly of FIG. 4.
Figure 19:
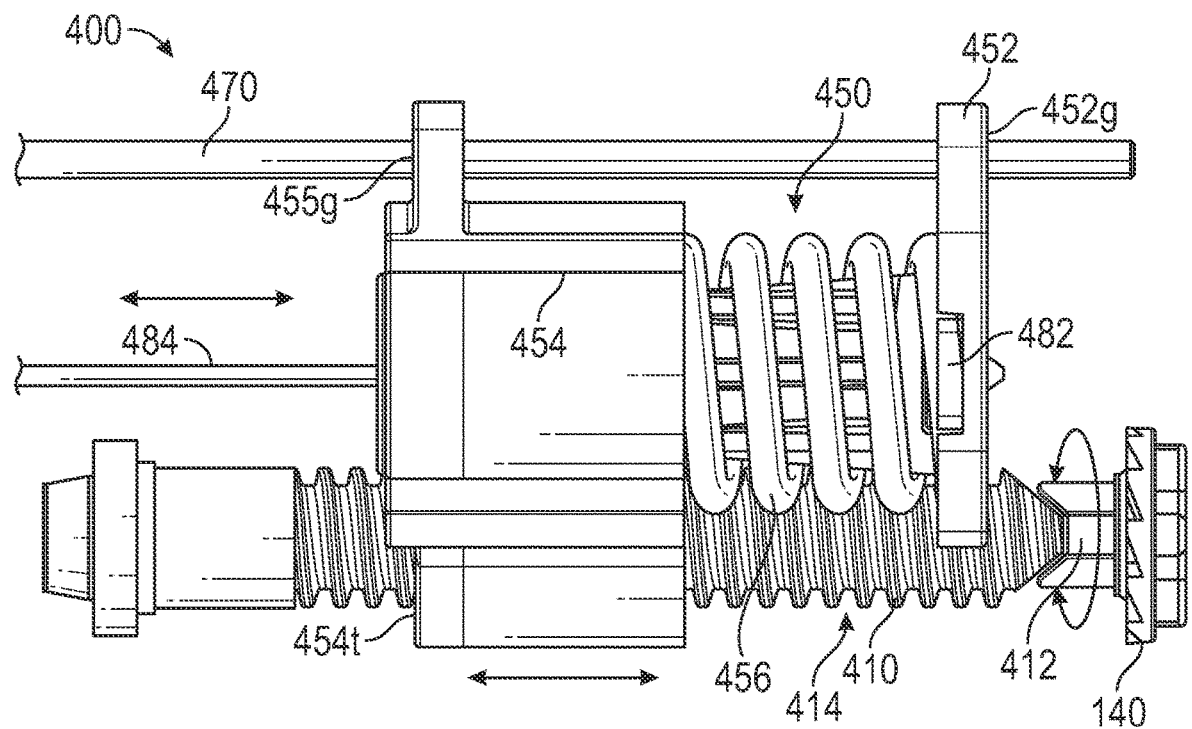
FIG. 19 is a side view of a jaw drive assembly of the gearbox assembly of the surgical instrument of FIG. 1A.
Figure 20:
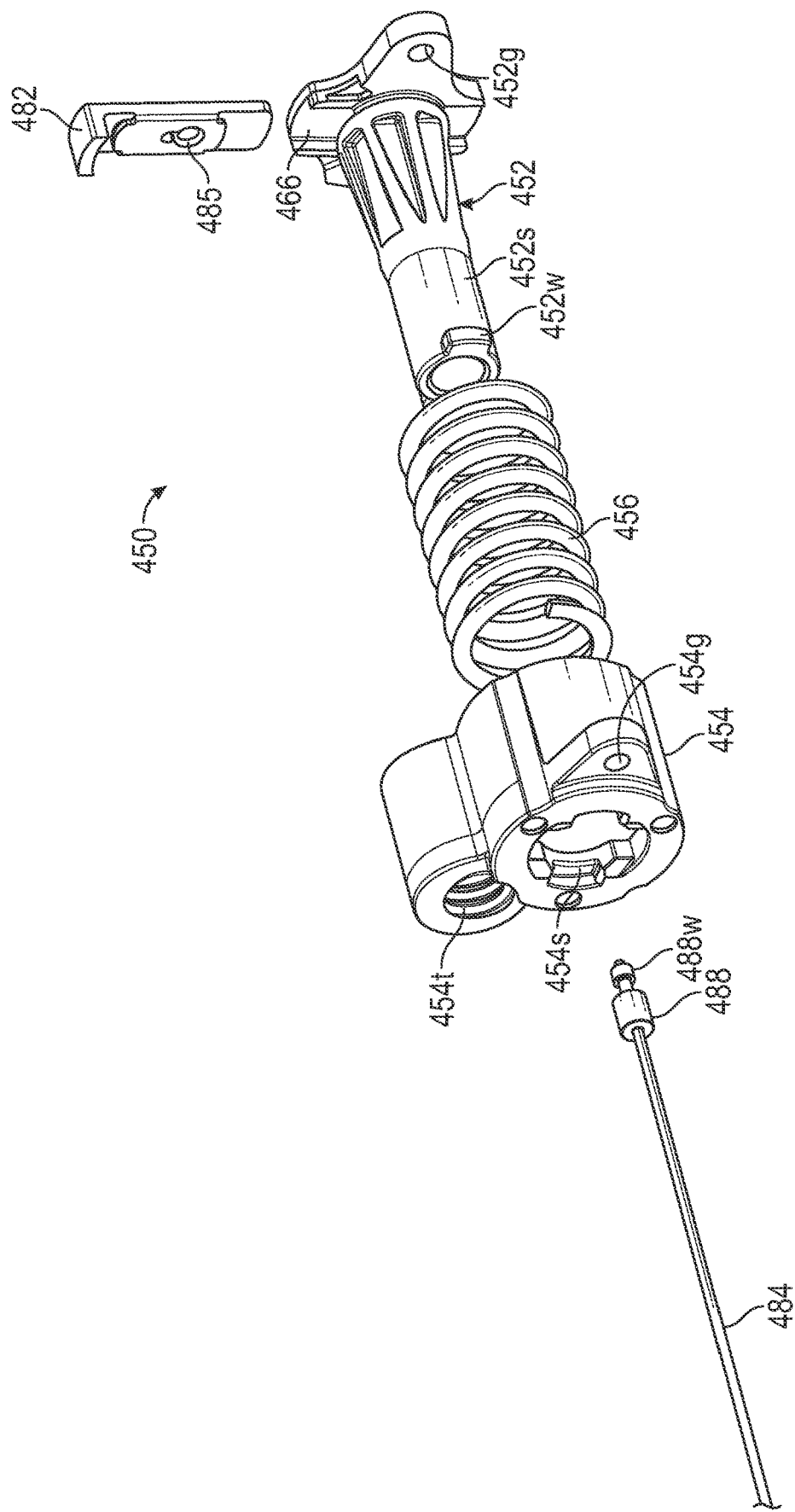
FIG. 20 is a front, perspective view of the jaw drive sub-assembly of FIG. 19 with parts separated and additional components removed.

With reference to FIGS. 3-18, articulation sub-assembly 200 of gearbox assembly 100 is shown generally including a first input shaft 202, a second input shaft 204, a proximal plate 230, a middle plate 250, a proximal center gear 222, and a distal center gear 224. The articulation sub-assembly 200 also includes a first lead screw 302 threadingly coupled to a first nut 312, a second lead screw 304 threadingly coupled to a second nut 314, a third lead screw 306 threadingly coupled to a third nut 316, and a fourth lead screw 308 threadingly coupled to a fourth nut 318. Rotation of lead screws 302, 304, 306, 308 effects longitudinal translation of the respective nut 312, 314, 316, 318 which are coupled to proximal portions of respective articulation cables 38 (FIG. 1A) to articulate end effector assembly 40 relative to a longitudinal axis "L" defined by shaft 30. In particular, each of nuts 312, 314, 316, 318 includes a cable connector 312c, 314c, 316c, 318c (FIG. 14) for coupling to a proximal portion of each articulation cable 38.

Middle plate 250 includes a middle plate stem 255 extending proximally therefrom for supporting the proximal center gear 222 and the distal center gear 224. Proximal center gear 222 is rotatable around the middle plate stem 255 and includes a proximal gear portion 222p and a distal gear portion 222d. Proximal gear portion 222p and distal gear portion 222d may have different diameters. The distal gear portion 222d of the proximal center gear 222 is meshingly engaged with a gear portion 302g of the first lead screw 302. Distal center gear 224 is rotatable around the middle plate stem 255 and includes a proximal gear portion 224p and a distal gear portion 224d. Proximal gear portion 224p and distal gear portion 224d may have different diameters. The distal gear portion 224d of the distal center gear 224 is meshingly engaged with a gear portion 304g of the second lead screw 304. The proximal gear portion 224p of the distal center gear 224 is aligned with the waist portion 302w of the first lead screw 302.

First input shaft 202 includes a gear portion 202g meshingly engaged with the proximal gear portion 222p of the proximal center gear 222 such that rotation of the first input shaft 202 causes rotation of the proximal center gear 222 and, in turn, the first lead screw 302. Second input shaft 204 includes a gear portion 204g meshingly engaged with the proximal gear portion 224p of the distal center gear 224 such that rotation of the second input shaft 204 causes rotation of the distal center gear 224 and, in turn, the second lead screw 304.

Third lead screw 306 includes a gear portion 306g, a waist portion 306w, and an elongate threaded body portion 306t. The gear portion 306g of the third lead screw 306 is meshingly engaged with the distal gear portion 222d of the proximal center gear 222 such that rotation of the proximal center gear 222 causes rotation of the third lead screw 306. The waist portion 306w of the third lead screw 306 is aligned with the proximal gear portion 224p of the distal center gear 224. As described above, third nut 316 is threadingly engaged with the elongate threaded body portion 306t of the third lead screw 306. With this configuration, rotation of the third lead screw 306, by means of rotation of the proximal center gear 222, effects longitudinal translation of the third nut 316.

Fourth lead screw 308 includes a gear portion 308g and an elongate threaded body portion 308t. The gear portion 308g of the fourth lead screw 308 is meshingly engaged with the distal gear portion 224d of the distal center gear 224 such that rotation of the distal center gear 224 causes rotation of the fourth lead screw 308. As described above, fourth nut 318 is threadingly engaged with the elongate threaded body portion 308t of the fourth lead screw 308. With this configuration, rotation of the fourth lead screw 308, by means of rotation of the distal center gear 224, effects longitudinal translation of the fourth nut 318.

Figure 8:
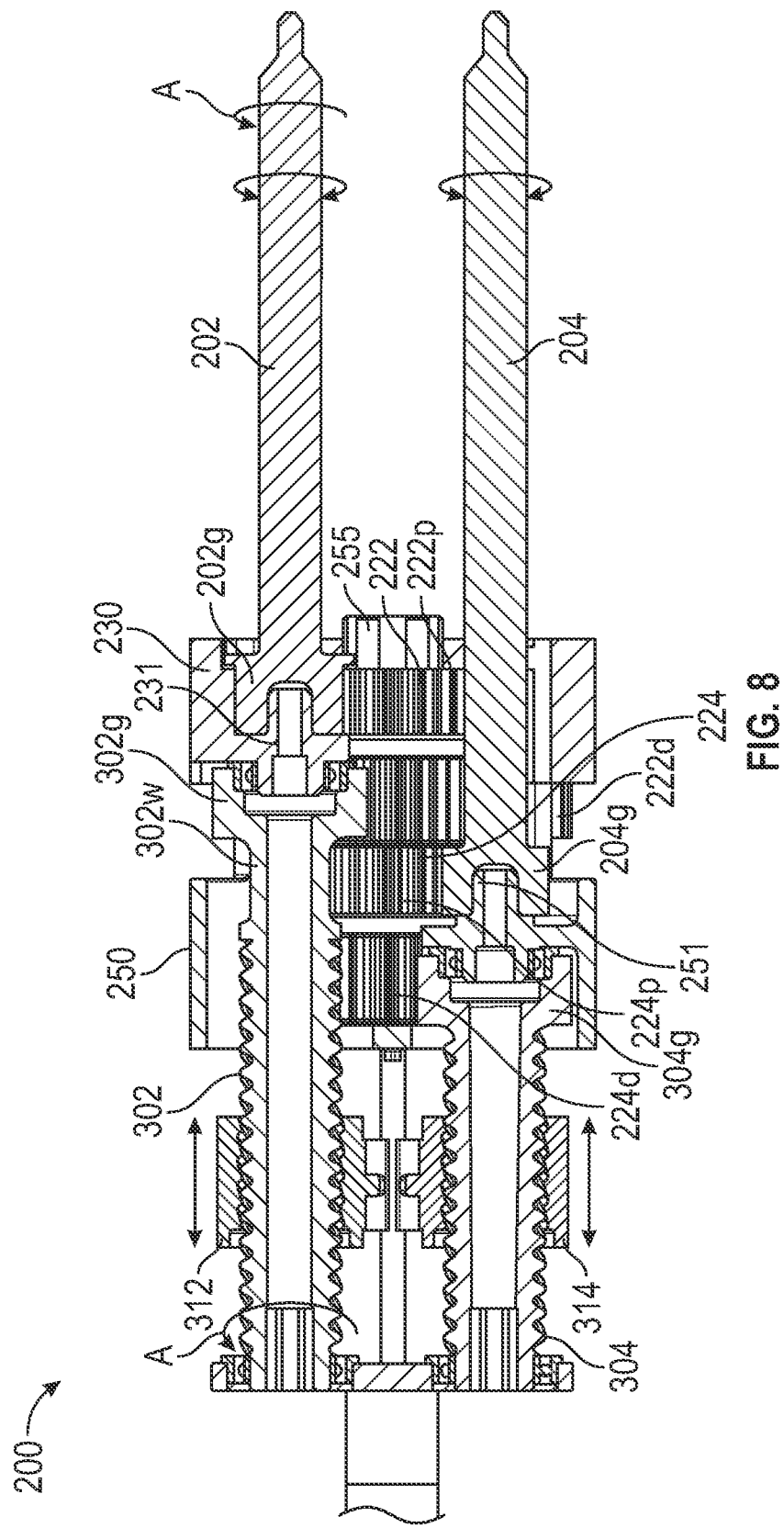
FIG. 8 is a top, cross-sectional view of the articulation sub-assembly of FIG. 4.
Figure 9:
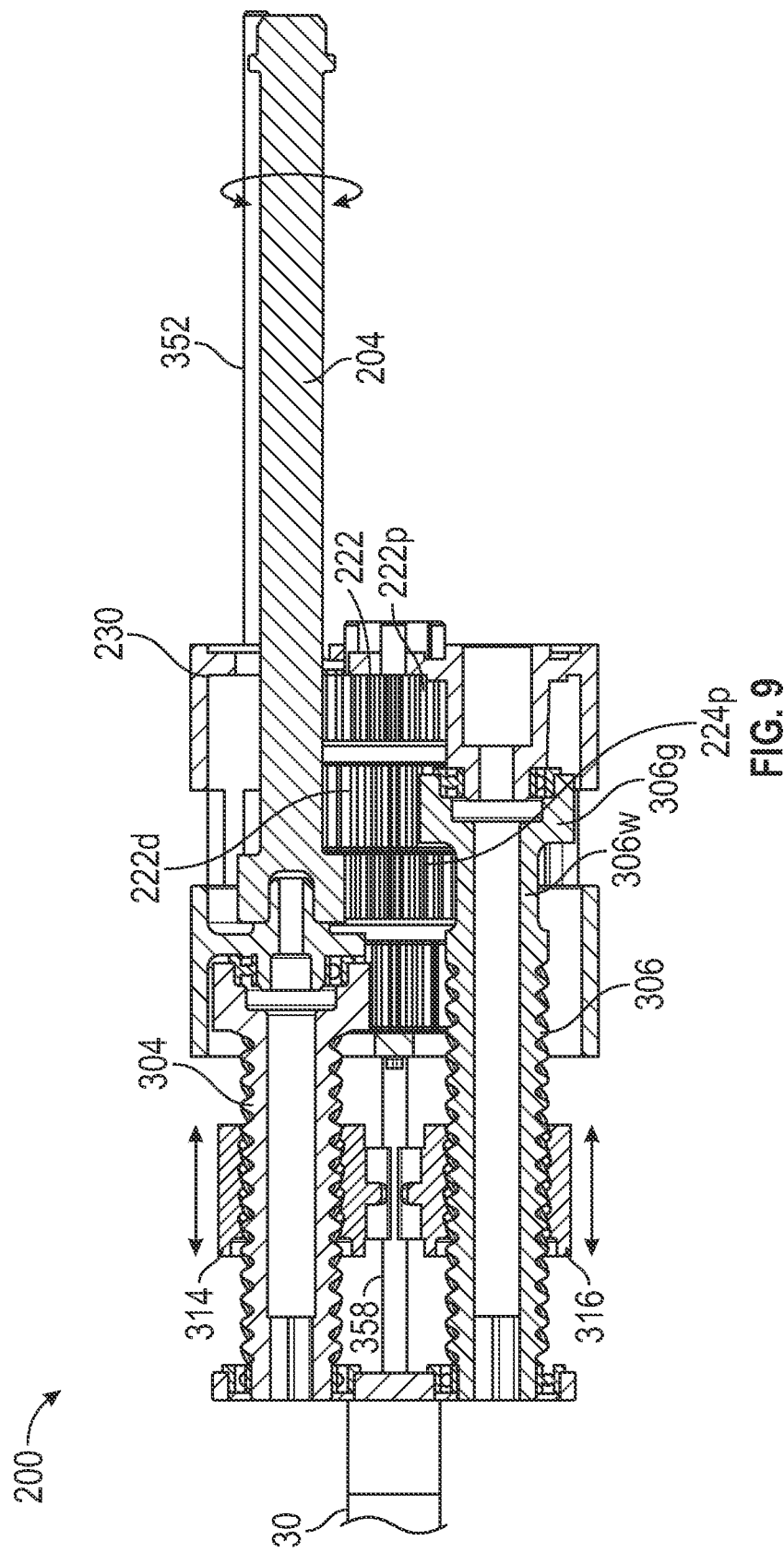
FIG. 9 is a side, cross-sectional view of the articulation sub-assembly of FIG. 4.
Figure 12:
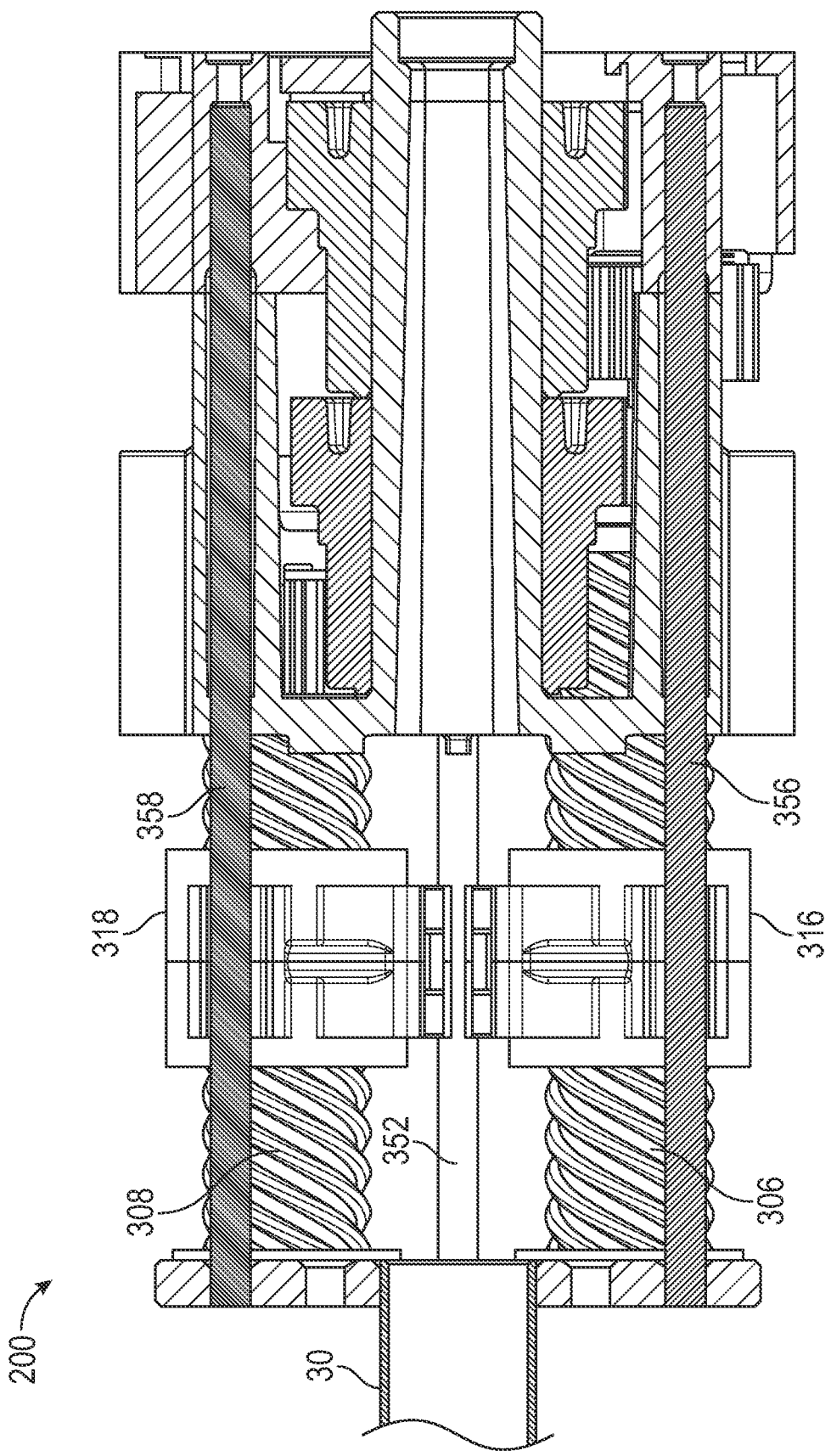
FIG. 12 is a top, cross-sectional view of the articulation sub-assembly of FIG. 4.
Figure 13:
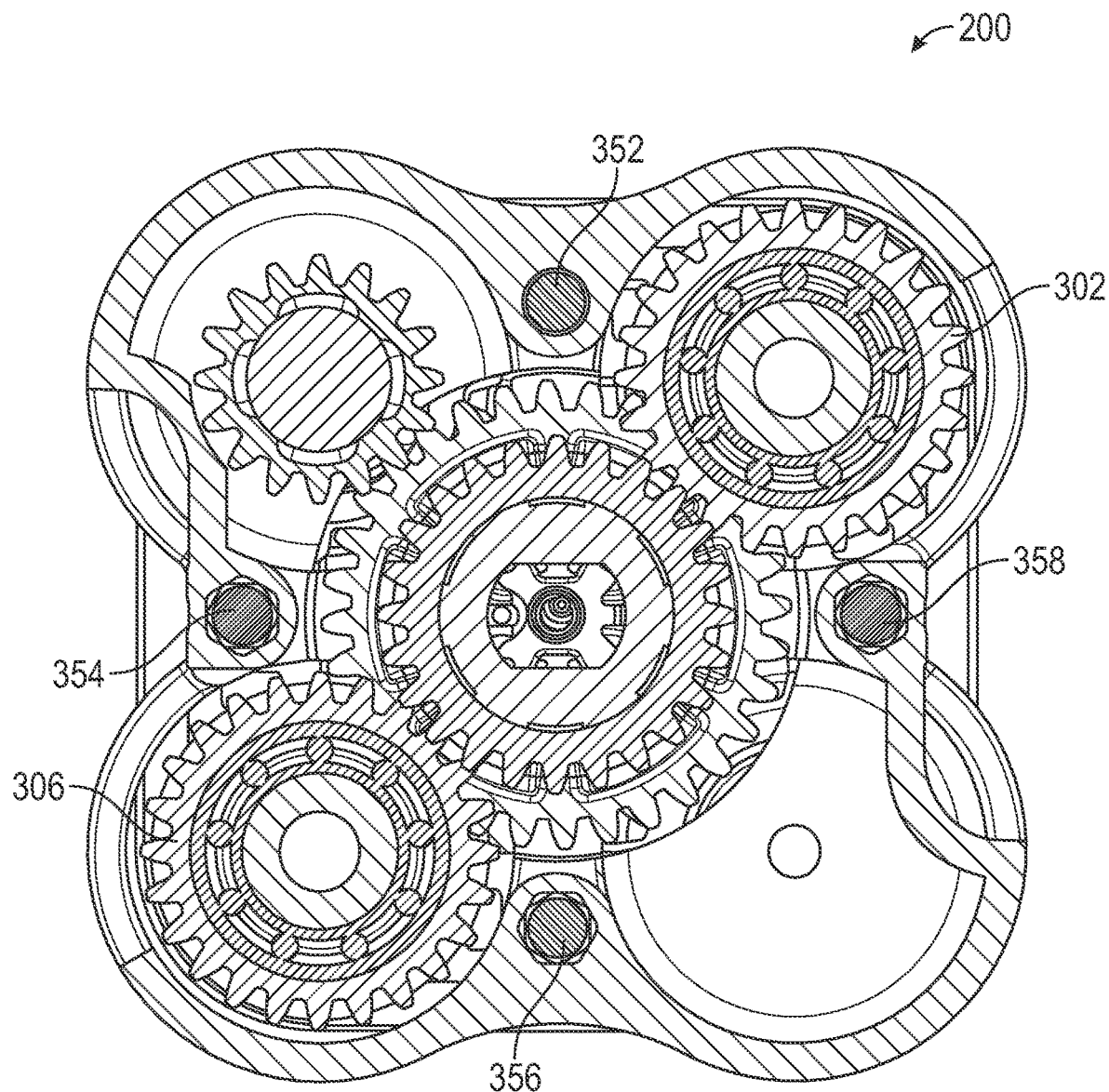
FIG. 13 is a front, cross-sectional view of the articulation sub-assembly of FIG. 4.

As best illustrated in FIG. 8, proximal plate 230 includes an alignment portion 231 which serves to maintain longitudinal alignment between the first input shaft 202 and the first lead screw 302. Similarly, middle plate 250 includes an alignment portion 251 which serves to maintain longitudinal alignment between the second input shaft 204 and the second lead screw 304.

Articulation sub-assembly 200 also includes guide bars 352, 354, 356, 358 which serve to maintain alignment between the internal components to which they are coupled and to prevent rotation of nuts 312, 314, 316, 318 as lead screws 302, 304, 306, 308 are rotated. In particular, a first guide bar 352 is disposed within the housing 20 and is operably coupled to the middle plate 250 and the first nut 312. The first guide bar 352 inhibits rotation of the first nut 312 relative to the first lead screw 302 during rotation of the first lead screw 302 thereby enabling longitudinal translation of the first nut 312 therealong. A second guide bar 354 is also disposed within the housing 20 and is operably coupled to the middle plate 250 and the second nut 314. The second guide bar 354 is configured to inhibit rotation of the second nut 314 relative to the second lead screw 304 during rotation of the second lead screw 302 thereby enabling longitudinal translation of the second nut 314 therealong. Additionally, a third guide bar 356 is disposed within the housing 20 and is operably coupled to the middle plate 250 and the third nut 316. The third guide bar 356 is configured to inhibit rotation of the third nut 316 relative to the third lead screw 306 during rotation of the third lead screw 306 thereby enabling longitudinal translation of the third nut 316 therealong. Finally, a fourth guide bar 358 is also disposed within the housing 20 and is operably coupled to the middle plate 250 and the fourth nut 318. The fourth guide bar 358 inhibits rotation of the fourth nut 318 relative to the fourth lead screw 308 during rotation of the fourth lead screw 308 thereby enabling longitudinal translation of the fourth nut 318 therealong.

Although described above as one guide bar being coupled to one nut for inhibiting rotation of the nut, more than one guide bar may be coupled to a single nut, for example, two guide bars to inhibit a single nut's rotation. For example, first guide bar 352 and second guide bar 354 may be operably coupled to the first nut 312 for inhibiting rotation of the first nut 312, second guide bar 354 and third guide bar 356 may be operably coupled to the second nut 314 for inhibiting rotation of the second nut 314, third guide bar 356 and fourth guide bar 358 may be operably coupled to the third nut 316 for inhibiting rotation of the third nut 316, and fourth guide bar 358 and first guide bar 352 may be operably coupled to the fourth nut 318 to inhibit rotation of the fourth nut 318.

As described above, with respect to articulation of end effector assembly 40 relative to proximal segment 34 of shaft 30, actuation of articulation cables 38 may be effected in pairs. More specifically, in order to pitch end effector assembly 40, the upper pair of cables 38 are actuated in a similar manner while the lower pair of cables 38 are actuated in a similar manner relative to one another but an opposite manner relative to the upper pair of cables 38. With respect to yaw articulation, the right pair of cables 38 are actuated in a similar manner while the left pair of cables 38 are actuated in a similar manner relative to one another but an opposite manner relative to the right pair of cables 38. Such actuation (e.g., pulling or providing slack) of articulation cables 38 are caused by the rotation of first input shaft 202 and second input shaft 204, which through the geared coupling of the components of articulation sub-assembly 200 described above, ultimately effect longitudinal translation of each of nuts 312, 314, 316, 318 which are coupled to respective proximal portions of articulation cables 38.

As described above, end effector assembly 40 includes a first jaw member 42 and a second jaw member 44 with the first jaw member 42 movable relative to the second jaw member 44 between an open position and a closed position to grasp tissue therebetween. Jaw drive sub-assembly 400 is operably coupled to at least one of the first jaw member 42 or the second jaw member 44 and is configured to move the first jaw member 42 relative to the second jaw member 44 between the open position and the closed position.

With reference to FIGS. 19-25, jaw drive sub-assembly 400 of gearbox assembly 100 is shown generally including an input shaft 410, a spring force assembly 450 operably coupled to the input shaft 410, and a drive rod 484 operably coupled to the input shaft 410 via the spring force assembly 450. In particular, a proximal portion of drive rod 484 is coupled to the spring force assembly 450 and a distal portion of drive rod 484 is coupled to one of first jaw member 42 or second jaw member 44 such that longitudinal translation of the spring force assembly 450 (or one or more of its components) pushes or pulls the drive rod 484 to move at least one of the first jaw member 42 or the second jaw member 44 relative to the other. The spring force assembly 450 is configured to maintain a jaw force between the first jaw member 42 and the second jaw member 44 during articulation of the end effector assembly 40.

Input shaft 410 includes a proximal end portion 412 operably coupled to third input 130 (FIG. 1B) such that rotation of third input 130 effects rotation of input shaft 410. That is, rotational input provided to third input 130 drives rotation of input shaft 410. Spring force assembly 450 is coupled to input shaft 410 and includes a proximal hub 452, a distal hub 454, a compression spring 456, and a lock plate 482. Spring force assembly 450 may further include a guide bar 470, or alternatively may be coupled to any of guide bars 352, 354, 356, 358 described above.

Figure 23:
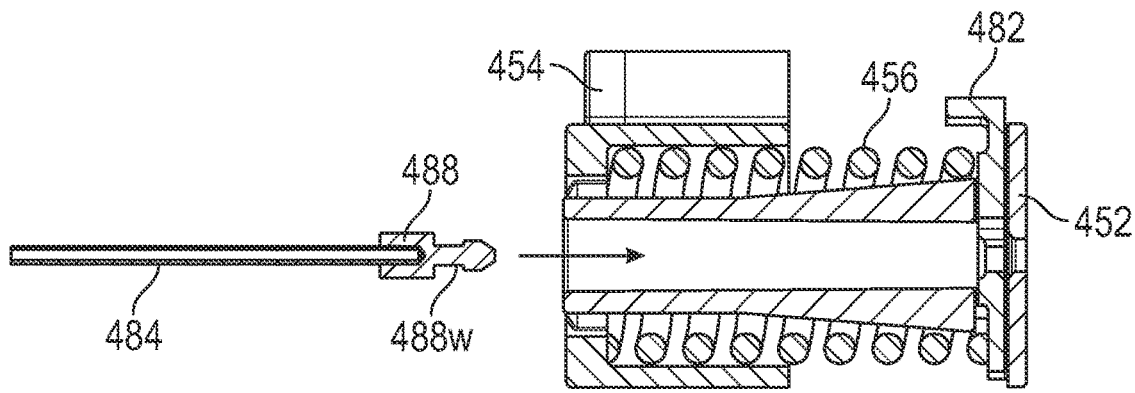
FIG. 23 is a side, cross-section view of the jaw drive sub-assembly of FIG. 19 prior to insertion of a drive rod through the proximal hub.
Figure 24:
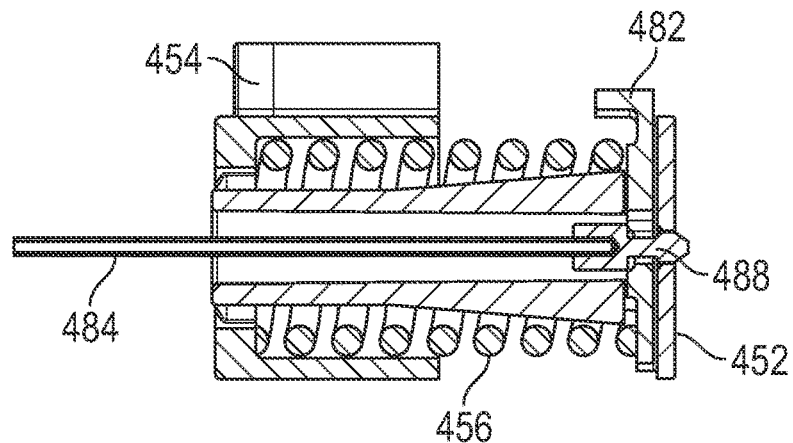
FIG. 24 is a side, cross-sectional view of the jaw drive sub-assembly of FIG. 19 after insertion of the drive rod through the proximal hub.
Figure 25:
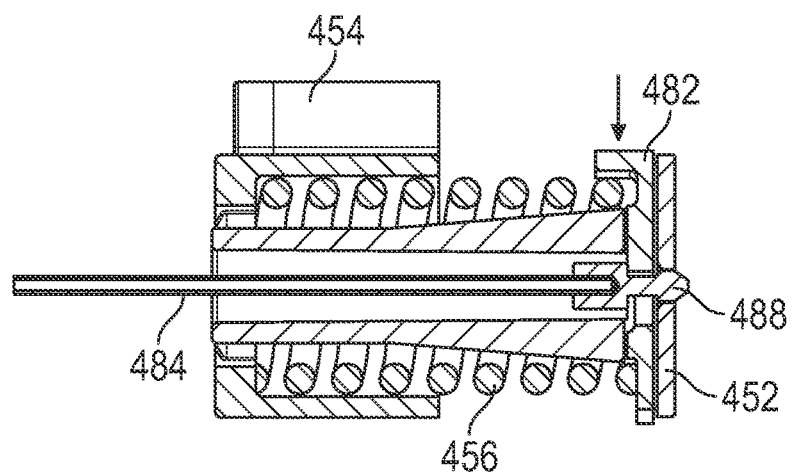
FIG. 25 is a side, cross-sectional view of the jaw drive sub-assembly of FIG. 19 after insertion of the drive rod through the proximal hub and securement thereto.

Proximal hub 452 includes a transverse slot 466 defined therethrough that is configured to receive lock plate 482, as detailed below, to fix lock plate 482 and, thus, a proximal end portion of drive rod 484 relative to proximal hub 452 (see FIGS. 23-25). Once engaged in this manner, drive rod 484 is locked in position and coaxially disposed through proximal hub 452, and distal hub 454. In particular, a proximal portion of the drive rod 484 includes a key 488 and the lock plate 482 defines a key hole 485 configured to receive the key 488 to releasably secure the drive rod 484 to the proximal hub 452.

Compression spring 456 is disposed around an elongate hub stem 452s of proximal hub 452. Distal hub 454 is disposed around a distal portion of the compression spring 456 and movable relative to the proximal hub 452 with the biasing force provided by the compression spring 456 positioned therebetween. A distal portion of the elongate hub stem 452s includes a wing 452w extending radially outward therefrom which is configured to engage a shelf 454s of the distal hub 454. With this configuration, distal translation of the distal hub 454 is inhibited beyond the wing 452w thereby defining a maximum distance between the proximal hub 452 and the distal hub 454.

Figure 21:
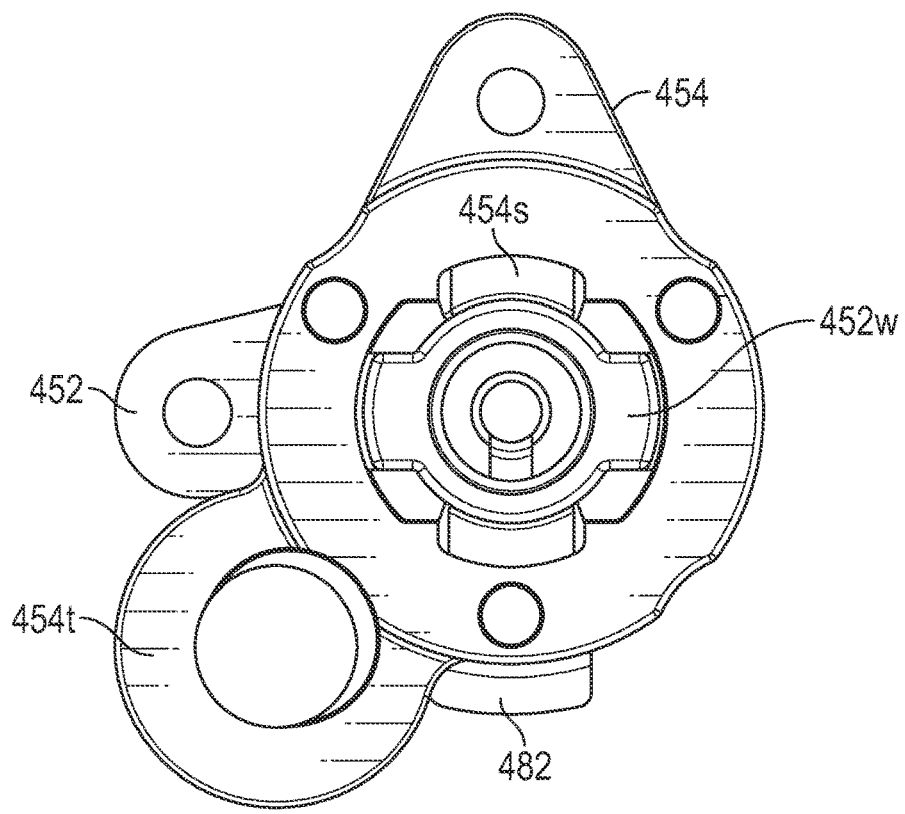
FIG. 21 is a front view of a proximal hub prior to securement to a distal hub of the jaw drive sub-assembly of FIG. 19.
Figure 22:
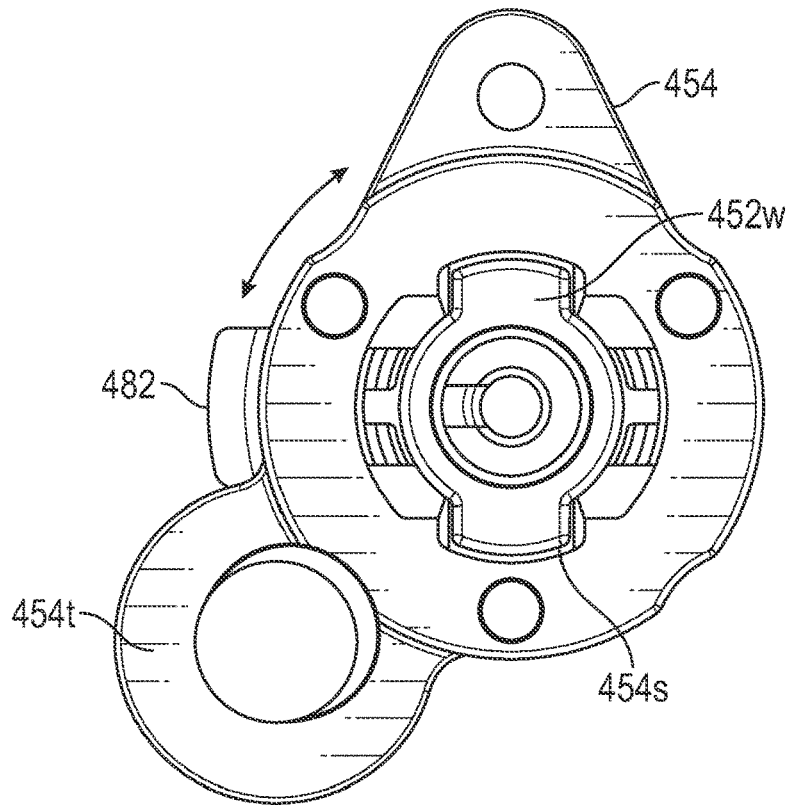
FIG. 22 is a front view of the proximal hub after securement to the distal hub of the jaw drive sub-assembly of FIG. 19.

With reference to FIGS. 21 and 22, elongate hub stem 452s of proximal hub 452 is positioned through an opening defined by the distal hub 454 while in a first orientation and then is turned, for example a quarter turn, relative to the distal hub 454 to engage the shelf 454s of the distal hub 454 to the wing 452w of the proximal hub 452. The compression spring 456 provides an outward force against the distal hub 454 to maintain engagement between the shelf 454s of the distal hub 454 to the wing 452w of the proximal hub 452.

An elongate threaded body portion 414 of input shaft 410 is threadingly engaged with a threaded bore 454t of the distal hub 454 such that rotation of the input shaft 410 causes longitudinal translation of the distal hub 454. Each of a retainer guide 452g of the proximal hub 452 and a retainer guide 454g of the distal hub 454 are operably coupled to a guide bar 470 to inhibit rotation of the distal hub 454 relative to the proximal hub 452 and maintain alignment therebetween as the input shaft 410 is rotated.

In use, jaw members 42, 44 are initially disposed in the open position and, correspondingly, proximal and distal hubs 452, 454 are disposed in a distal-most position such that drive rod 484 is disposed in a distal-most position. Further, in this position, compression spring 456 is disposed in a least-compressed condition; although, as noted above, even in the least-compressed condition, compression spring 456 is partially compressed due to the retention of compression spring 456 between proximal and distal hubs 452, 454.

In response to an input to close end effector assembly 40, e.g., rotational input to third input 130, input shaft 410 is rotated such that distal hub 454 is translated proximally towards proximal hub 452. Proximal translation of distal hub 454 urges distal hub 454 against compression spring 456. Initially, where forces resisting approximation of jaw members 42, 44 are below a threshold corresponding to the spring value of compression spring 456, the closure force applied by jaw members 42, 44 is relatively low such that the urging of distal hub 454 proximally against compression spring 456 urges compression spring 456 proximally which, in turn, urges proximal hub 452 and lock plate 482 and, thus, drive rod 484 proximally to pivot first jaw member 42 relative to second jaw member 44 from the spaced-apart position towards the approximated position to grasp tissue therebetween.

Upon further approximation of jaw members 42, 44 to grasp tissue therebetween, the forces resisting approximation of jaw members 42, 44, e.g., tissue resisting compression, may reach the threshold and, thus the closure force applied by jaw members 42, 44 may reach a corresponding threshold. In order to maintain the closure force applied by jaw members 42, 44 within a closure force range such as, for example, from about 3 kg/cm$^2$ to about 16 kg/cm$^2$, application of further closure force by jaw members 42, 44 is inhibited beyond this point despite further rotational input to third input 130. More specifically, once the threshold has been reached, further rotational input to third input 130 rotates input shaft 410 to translate distal hub 454 further proximally into compression spring 456. However, rather than compression spring 456 urging proximal hub 452 further proximally to continue approximation of jaw members 42, 44 and increase the closure force applied therebetween, compression spring 456 is compressed, enabling proximal hub 452 and, thus, drive rod 484 to remain in position, thus inhibiting application of additional closure force between jaw members 42, 44.

With tissue grasped between jaw members 42, 44 under an appropriate closure force, energy may be supplied to jaw members 42, 44 to treat (e.g., seal) tissue. Thereafter, the knife blade (not shown) may be advanced between jaw members 42, 44 to cut the treated tissue.

Once tissue is cut or otherwise treated or grasped, an opposite rotation input is provided to fourth input 140 to return the knife blade (not shown) to its initial position proximally of body portions 43b, 45b of jaw members 42, 44 (see FIG. 1A). Thereafter, an opposite input is provided to third input 130 to return jaw members 42, 44 back towards the spaced-apart position to release the sealed, grasped, and/or cut tissue.

It will be understood that various modifications may be made to the aspects disclosed herein. Therefore, the above description should not be construed as limiting, but merely as exemplifications of various aspects. Those skilled in the art will envision other modifications within the scope and spirit of the claims appended thereto.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical instrument, comprising:
    an end effector including a first jaw member and a second jaw member, the first jaw member movable relative to the second jaw member between an open position and a closed position to grasp tissue therebetween; and
    a jaw drive sub-assembly configured to transition the end effector between the open position and the closed position, the jaw drive sub-assembly including:
        a drive rod operably coupled to the first jaw member; and
        a spring force assembly releasably coupled to the drive rod, the spring force assembly including:
            a proximal hub defining an elongate hub stem;
            a compression spring disposed around the elongate hub stem;
            a distal hub disposed around a distal portion of the compression spring and movable relative to the proximal hub; and
            a lock plate slidingly coupled to the proximal hub and configured to releasably lock the drive rod to the proximal hub.

2. The surgical instrument of claim 1, wherein a distal portion of the elongate hub stem includes a wing extending radially outward therefrom and the distal hub defines a shelf configured to engage the wing to inhibit distal translation of the distal hub beyond the wing thereby defining a maximum distance between the proximal hub and the distal hub.

3. The surgical instrument of claim 1, wherein the jaw drive sub-assembly includes an input shaft having an elongate threaded body portion threadingly engaged with a threaded bore of the distal hub such that rotation of the input shaft causes longitudinal translation of the distal hub.

4. The surgical instrument of claim 1, wherein the proximal hub includes a retainer guide and the distal hub includes a retainer guide, each of the retainer guide of the proximal hub and the retainer guide of the distal hub configured to operably couple to a guide bar to inhibit rotation of the distal hub relative to the proximal hub.

5. The surgical instrument of claim 1, wherein the spring force assembly is configured to maintain a jaw force between the first jaw member and the second jaw member during articulation of the end effector.

6. The surgical instrument of claim 1, wherein a proximal portion of the drive rod includes a key and the lock plate defines a key hole configured to receive the key to releasably secure the drive rod to the proximal hub.

7. A gearbox assembly for use with a surgical instrument, the gearbox assembly comprising:
    an articulation sub-assembly configured to articulate an end effector including a first jaw member and a second jaw member of the surgical instrument; and
    a jaw drive sub-assembly configured to transition the end effector between an open position and a closed position, the jaw drive sub-assembly including:
        a drive rod operably coupled to at least one of the first jaw member or the second jaw member;
        a spring force assembly releasably coupled to the drive rod, the spring force assembly including:
            a proximal hub defining an elongate hub stem;
            a compression spring disposed around the elongate hub stem;
            a distal hub disposed around a distal portion of the compression spring and movable relative to the proximal hub; and
            a lock plate slidingly coupled to the proximal hub and configured to releasably lock the drive rod to the proximal hub.

8. The gearbox assembly of claim 7, wherein the articulation sub-assembly includes:
    a first lead screw including an elongate threaded body portion;
    a first nut threadingly engaged with the elongate threaded body portion of the first lead screw such that rotation of the first lead screw effects longitudinal translation of the first nut;
    a second lead screw including an elongate threaded body portion;
    a second nut threadingly engaged with the elongate threaded body portion of the second lead screw such that rotation of the second lead screw effects longitudinal translation of the second nut; and
    articulation cables including respective distal ends coupled to the end effector and respective proximal ends coupled to one of the first nut or the second nut such that longitudinal translation of the first nut and the second nut causes articulation of the end effector.

9. The gearbox assembly of claim 8, wherein the articulation sub-assembly includes:
    a middle plate including a middle plate stem extending proximally therefrom;
    a proximal center gear operably coupled to the middle plate stem and including a proximal gear portion and a distal gear portion, the distal gear portion of the proximal center gear meshingly engaged with the first lead screw; and a distal center gear operably coupled to the middle plate stem and including a proximal gear portion and a distal gear portion, the distal gear portion of the distal center gear meshingly engaged with the second lead screw and the proximal gear portion of the distal center gear aligned with the first lead screw.

10. The gearbox assembly of claim 7, wherein a distal portion of the elongate hub stem includes a wing extending radially outward therefrom and the distal hub defines a shelf configured to engage the wing to inhibit distal translation of the distal hub beyond the wing thereby defining a maximum distance between the proximal hub and the distal hub.

11. The gearbox assembly of claim 7, wherein the jaw drive sub-assembly includes an input shaft having an elongate threaded body portion threadingly engaged with a threaded bore of the distal hub such that rotation of the input shaft causes longitudinal translation of the distal hub.

12. The gearbox assembly of claim 7, wherein the proximal hub includes a retainer guide and the distal hub includes a retainer guide, each of the retainer guide of the proximal hub and the retainer guide of the distal hub configured to operably couple to a guide bar to inhibit rotation of the distal hub relative to the proximal hub.

13. The gearbox assembly of claim 7, wherein the spring force assembly is configured to maintain a jaw force between the first jaw member and the second jaw member during articulation of the end effector.

14. The gearbox assembly of claim 7, wherein a proximal portion of the drive rod includes a key and the lock plate defines a key hole configured to receive the key to releasably secure the drive rod to the proximal hub.

15. The gearbox assembly of claim 7, further comprising a guide bar operably coupled to the articulation sub-assembly and the jaw drive sub-assembly and configured to maintain alignment therebetween.

16. A surgical instrument, comprising:
an articulation sub-assembly configured to articulate an end effector including a first jaw member and a second jaw member of the surgical instrument, the articulation sub-assembly including:
 a first lead screw including an elongate threaded body portion;
 a first nut threadingly engaged with the elongate threaded body portion of the first lead screw such that rotation of the first lead screw effects longitudinal translation of the first nut;
 a second lead screw including an elongate threaded body portion;
 a second nut threadingly engaged with the elongate threaded body portion of the second lead screw such that rotation of the second lead screw effects longitudinal translation of the second nut; and
 articulation cables including respective distal ends coupled to the end effector and respective proximal ends coupled to one of the first nut and the second nut such that longitudinal translation of the first nut and the second nut causes articulation of the end effector; and
a jaw drive sub-assembly configured to transition the end effector between an open position and a closed position.

17. The surgical instrument of claim 16, wherein the jaw drive sub-assembly includes:
a drive rod operably coupled to at least one of the first jaw member or the second jaw member; and
a spring force assembly releasably coupled to the drive rod, the spring force assembly including:
 a proximal hub defining an elongate hub stem;
 a compression spring disposed around the elongate hub stem; and
 a distal hub disposed around a distal portion of the compression spring and movable relative to the proximal hub.

18. The surgical instrument of claim 16, wherein the jaw drive sub-assembly is configured to maintain a jaw force between the first jaw member and the second jaw member during articulation of the end effector.

19. The surgical instrument of claim 16, wherein the articulation sub-assembly includes:
a middle plate including a middle plate stem extending proximally therefrom;
a proximal center gear operably coupled to the middle plate stem and including a proximal gear portion and a distal gear portion, the distal gear portion of the proximal center gear meshingly engaged with the first lead screw; and
a distal center gear operably coupled to the middle plate stem and including a proximal gear portion and a distal gear portion, the distal gear portion of the distal center gear meshingly engaged with the second lead screw.

20. The surgical instrument of claim 16, further comprising a guide bar operably coupled to the articulation sub-assembly and the jaw drive sub-assembly and configured to maintain alignment therebetween.

* * * * *